United States Patent
Flaherty et al.

(10) Patent No.: US 6,508,824 B1
(45) Date of Patent: Jan. 21, 2003

(54) CATHETER-BASED METHODS FOR ENLARGING BLOOD VESSELS TO FACILITATE THE FORMATION OF PENETRATION TRACTS, FISTULAS AND/OR BLOOD FLOW CHANNELS

(75) Inventors: J. Christopher Flaherty, Los Altos, CA (US); Theodore C. Lamson, Pleasanton, CA (US); John T. Garibotto, Palo Alto, CA (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 09/507,139

(22) Filed: Feb. 18, 2000

(51) Int. Cl.[7] .............................................. A61B 17/34
(52) U.S. Cl. ...................... 606/185; 600/464; 604/116; 606/194
(58) Field of Search ........................... 606/1, 108, 194, 606/195, 198, 200, 159, 170, 101.01, 101.05, 96.01, 103.07, 103.01, 185; 604/22, 115, 116; 600/464, 467, 470, 471

(56) References Cited

U.S. PATENT DOCUMENTS

| | | | | |
|---|---|---|---|---|
| 4,408,611 A | * | 10/1983 | Enjoji ......................... | 604/116 |
| 4,664,651 A | * | 5/1987 | Weinshenker et al. ...... | 604/115 |
| 5,830,222 A | * | 11/1998 | Makower .................... | 606/159 |
| 6,068,638 A | * | 5/2000 | Makower .................... | 606/159 |
| 6,283,942 B1 | * | 9/2001 | Stachlin et al. ............ | 604/116 |

* cited by examiner

*Primary Examiner*—Michael H. Thaler
(74) *Attorney, Agent, or Firm*—Robert D. Buyan; Stout, Uxa, Buyan & Mullins, LLP

(57) ABSTRACT

Methods, devices and systems wherein a penetrating catheter or other penetrating device is used to penetrate into a target blood vessel, and wherein the target vessel is dilated prior to the penetration so as to improve the imaging, aiming at and/or penetration into the target vessel. In one embodiment, a tissue penetrating catheter device that is useable to penetrate from a blood vessel in which it is positioned to a target vessel comprises a flexible catheter advanceable into the first blood vessel and a tissue penetrator lumen adapted to receive an operative tissue penetrator which is usable to penetrate from the blood vessel to the target vessel when properly aimed. An imaging transducer may be fixedly mounted on or within the penetrating catheter to provide an imaging signal from which an image of the target vessel can be obtained. A target vessel dilating catheter is inserted into the target vessel and used to dilate the target vessel prior to imaging, aiming of the penetrator at and/or puncture thereof. Such vessel dilating catheters may comprise one or more occlusion member(s) (e.g., one or two balloons) to block flow through the target vessel and/or to isolate and pressurize a region of the vessel. Alternatively, the dilating catheter may comprise a dilating member that expands within the target vessel to cause a portion of the target vessel wall to enlarge, stretch, expand, bulge or otherwise dilate.

21 Claims, 21 Drawing Sheets

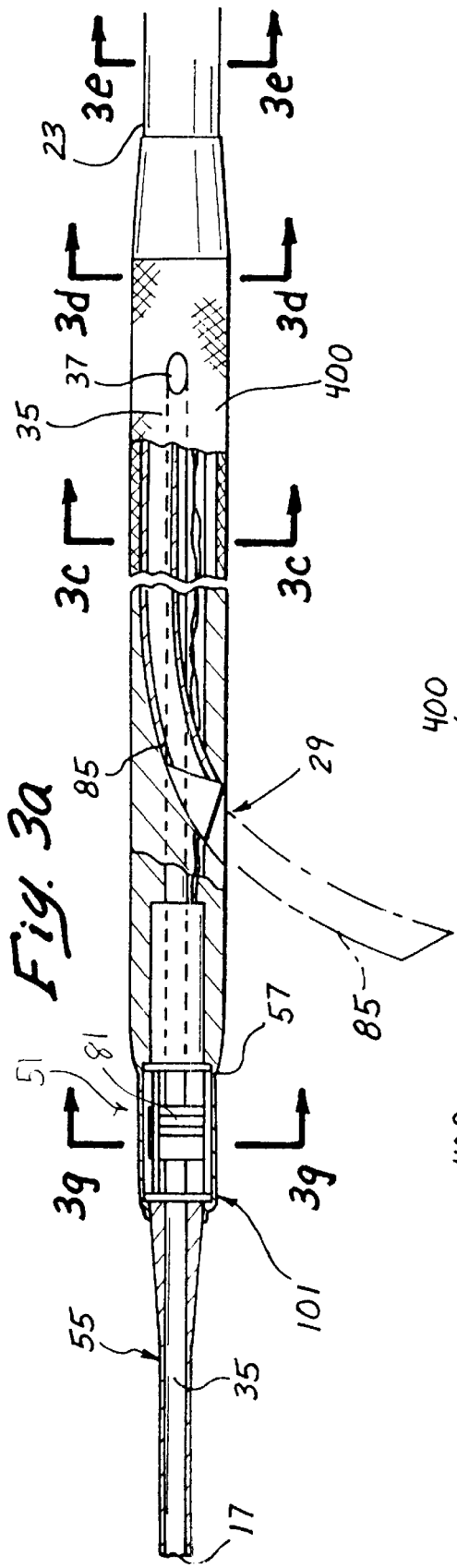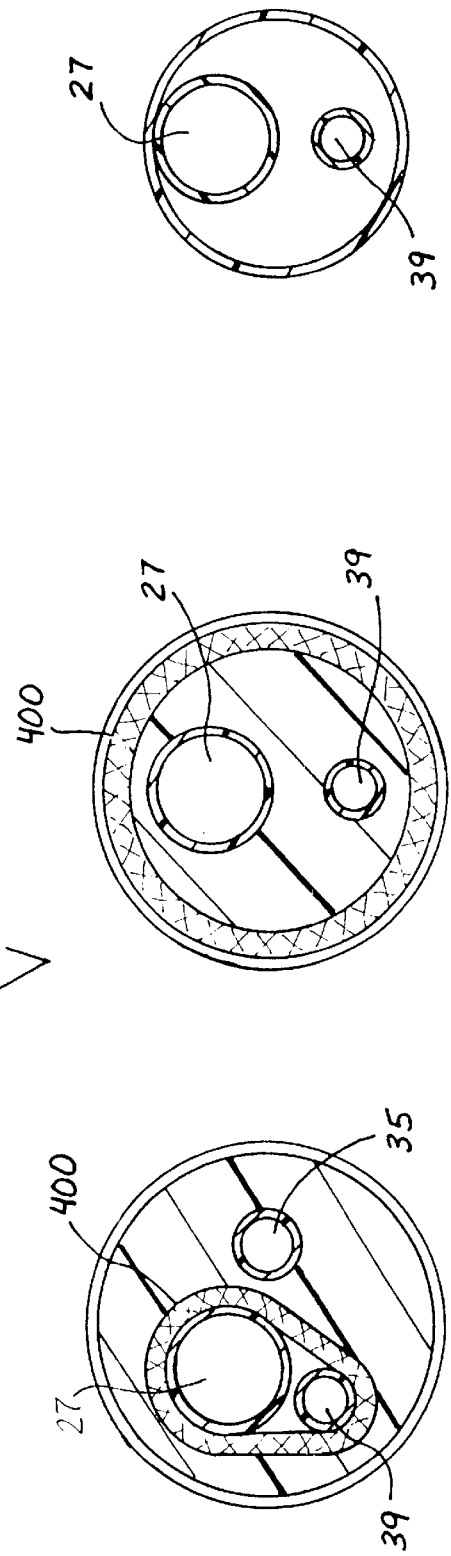

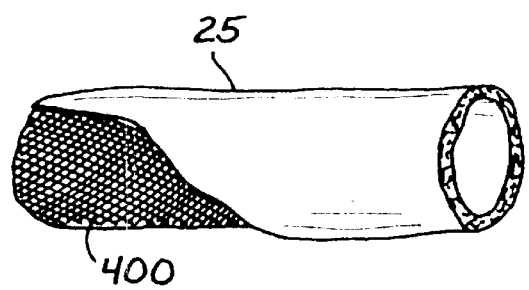
Fig. 3a'
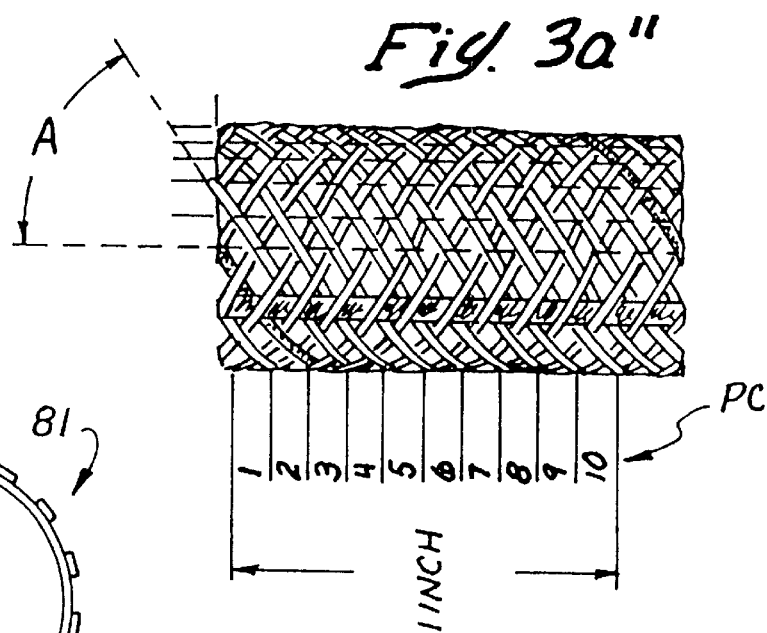
Fig. 3a"
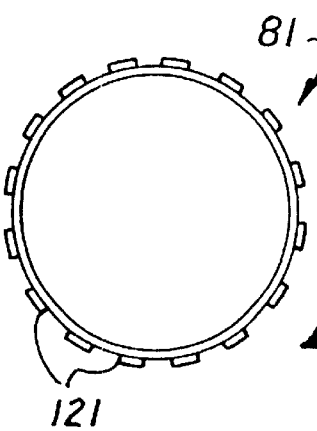
Fig. 4a
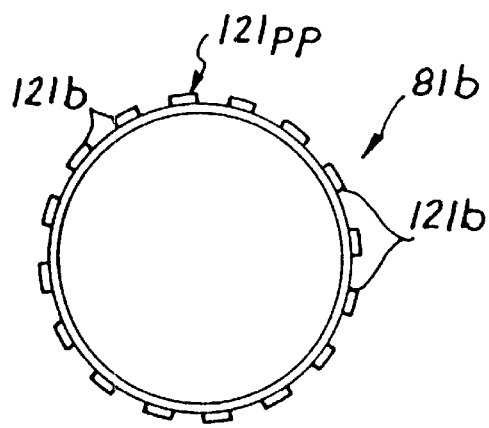
Fig. 4a'
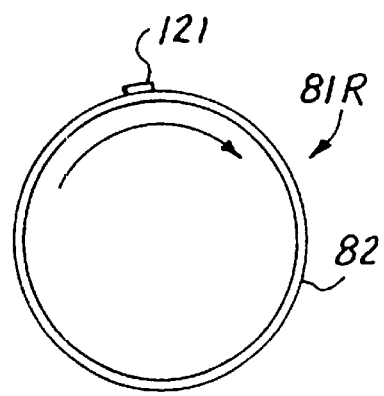
Fig. 4b

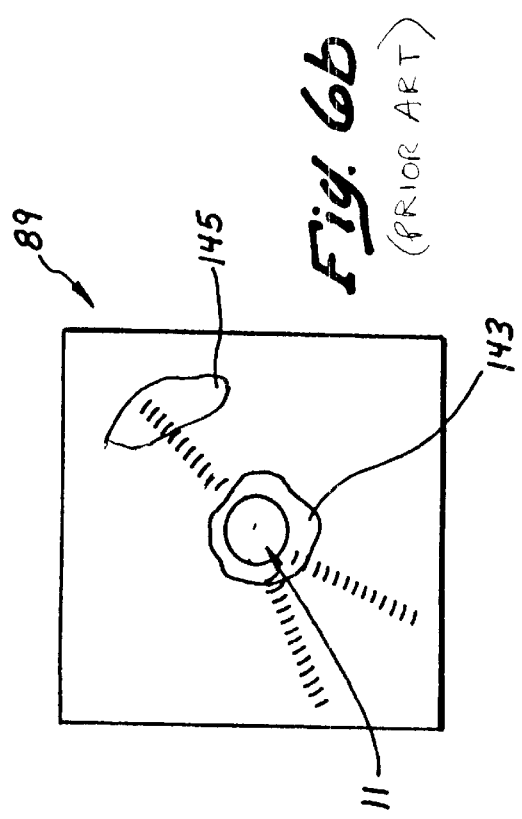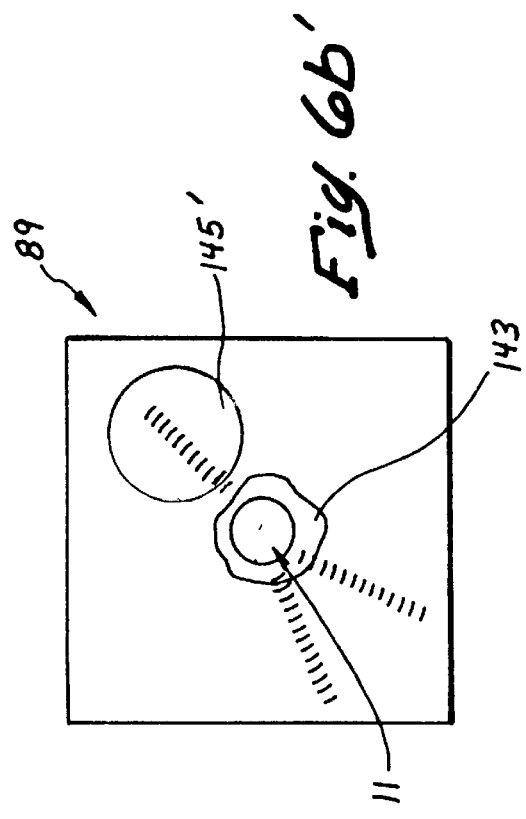
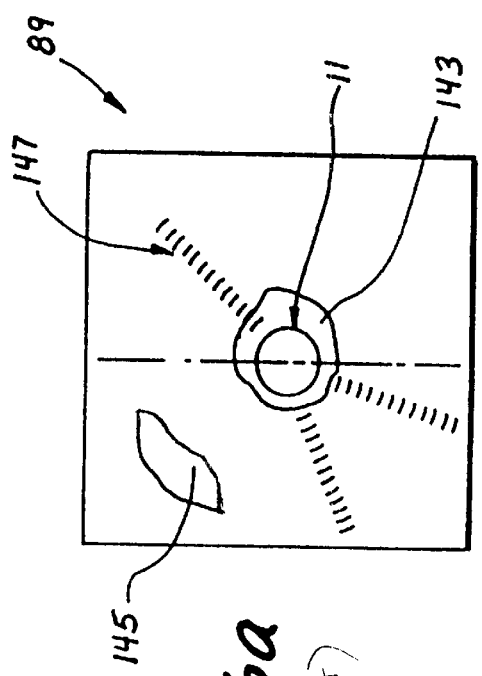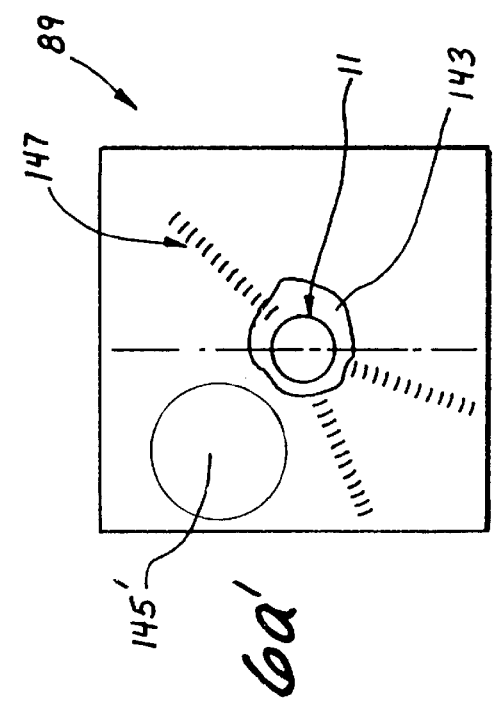
Fig. 6a (PRIOR ART)  Fig. 6a'
Fig. 6b (PRIOR ART)  Fig. 6b'

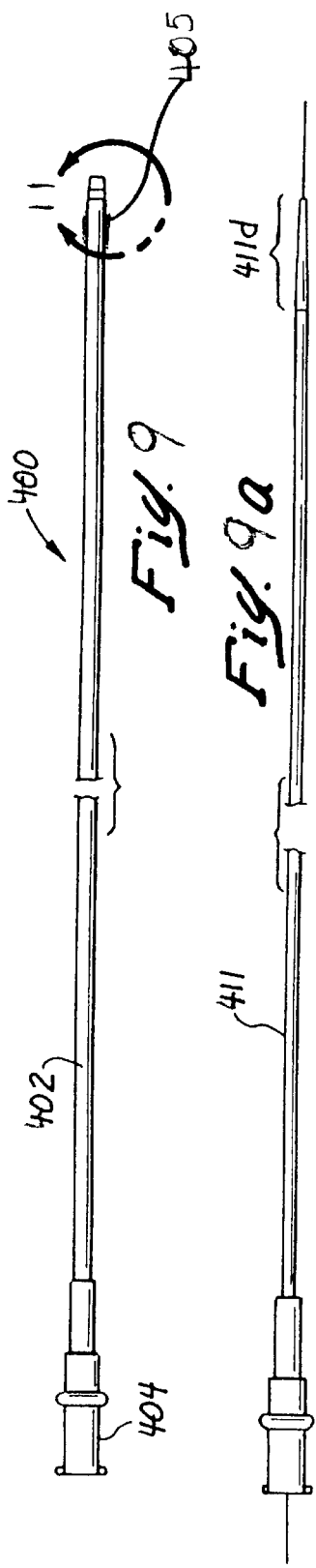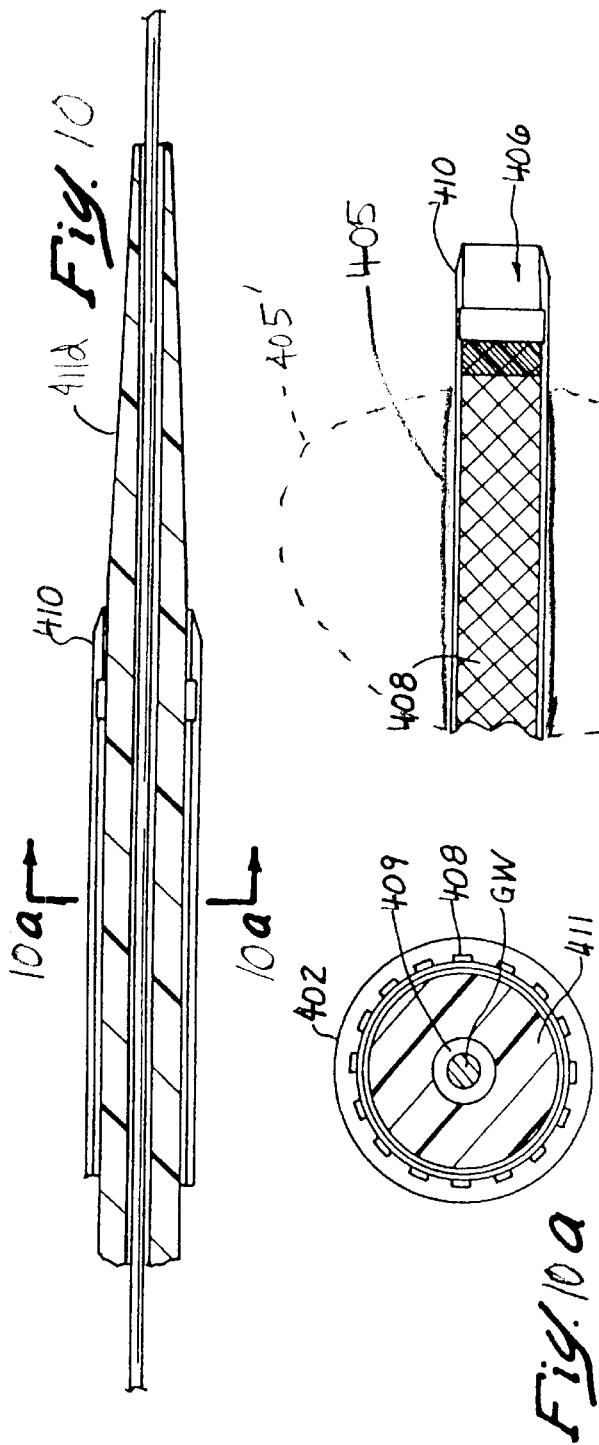

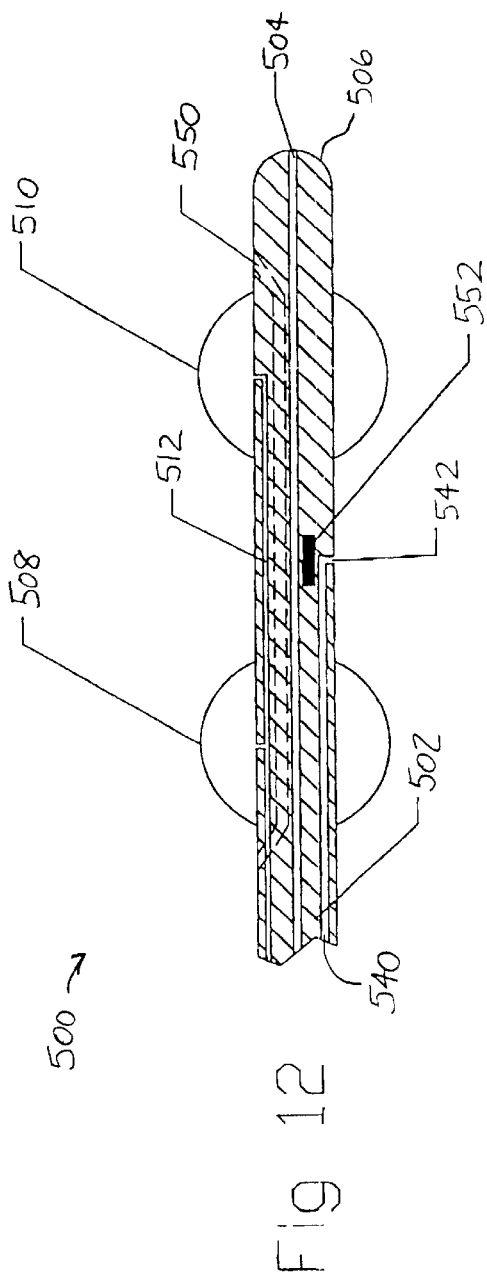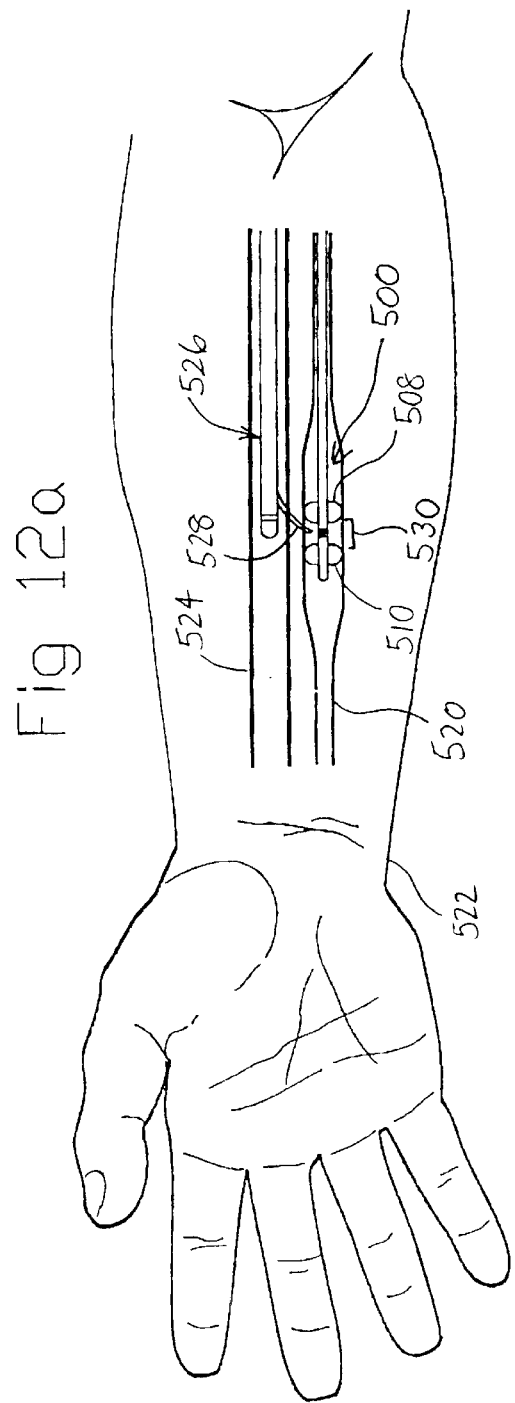

CATHETER-BASED METHODS FOR ENLARGING BLOOD VESSELS TO FACILITATE THE FORMATION OF PENETRATION TRACTS, FISTULAS AND/OR BLOOD FLOW CHANNELS

FIELD OF THE INVENTION

The present invention relates generally to medical devices and methods, and more particularly to catheter devices and methods that are useable to form penetration tracts, fistulas or blood flow channels into target vessels in furtherance of a therapeutic purpose such as bypassing an arterial blockage, arterializing a vein, creating a dialysis fistula, or performing other interventional procedures.

BACKGROUND OF THE INVENTION

In most regions of the world, atherosclerotic cardiovascular disease remains a major cause of premature death and morbidity. Various transluminal, catheter-based interventional techniques have been used, or proposed for use, to dilate or otherwise treat atherosclerotic obstructions that occur in coronary and/or peripheral arteries. These therapies have traditionally focused on treating the disease intraluminally, or from "within" the vessel lumen.

Included among the newer interventional techniques are certain percutaneous, transluminal techniques for bypassing obstructions in coronary or peripheral arteries through the use of the adjacent vein(s) as in situ bypass conduit(s); (e.g. using catheters to perform extra luminal procedures outside the diseased vessel lumen). These procedures include certain proprietary procedures known as PICVA™ and PICAB™ (PICVA™ and PICAB™ are trademarks of Transvascular, Inc. of Menlo Park, Calif.) as described in U.S. Pat. No. 5,830,222 (Makower) and in published PCT Applications WO 98/16161, WO 98/46119, WO99/49910 and WO99/49793. As described therein, in some instances, these procedures may be performed by a venous approach wherein a tissue penetrating catheter is inserted into a vein (the "host" vessel). The desired passageway or puncture is initially formed by facilitating the passage of a tissue penetrator (e.g., a flow of energy or an elongate penetration member) from the catheter, through the wall of the vein in which the catheter is positioned, and into a target location such as the lumen of an adjacent vessel (e.g. the artery). Alternatively, some of these procedures may be performed by an arterial approach wherein the catheter is inserted into an artery (the "host" vessel) and the desired passageway or puncture is initially formed by facilitating the passage of a tissue penetrator from the catheter, through the wall of the artery in which the catheter is positioned, and into the target location such as the lumen of an adjacent vessel (e.g. a vein). In some instances, the target vessel may be an artery.

In these procedures, the tissue-penetrating catheter must be placed in the proper longitudinal position and rotational orientation with respect to the target vessel prior to actuation or advancement of the tissue penetrator, to ensure that the tissue penetrator is aimed or positioned to enter the target vessel. To facilitate such aiming of the tissue penetrator, the tissue penetrating catheter may incorporate, or may be used in conjunction with, an imaging apparatus such as an intravascular ultrasound (IVUS) imaging apparatus to image the target vessel and possibly other structures. The image so obtained is then used to guide the longitudinal positioning and rotational orientation of the tissue penetrating catheter within the host vessel such that the penetrator will be aligned with the target and advancement or actuation of the tissue penetrator will result in the formation of the desired penetration tract between the host vessel and the target vessel.

Other techniques may also utilize a tissue penetrating catheter for infusion of medication into a vessel or other location, to place a guidewire into a vessel or other location, to form a channel into a vessel or other location through which other medical devices may be passed. For example, the tissue penetrating catheter may be inserted into any body cavity, such as the peritoneal cavity, adjacent a target vessel and the tissue penetrator used to access the target vessel. Indeed, certain procedures may be initiated from outside the body, with a tissue penetrating catheter or device used to penetrate into or gain access to a target vessel or other location within the body.

Various factors make accurate location of and subsequent penetration into a target vessel or other target location problematic. For example, although the general position of a target vessel or other target location may be known (e.g., certain coronary veins are expected to run parallel to certain coronary arteries), the anatomy of each patient may differ widely. Consequently, there is a need for a more accurate and repeatable technique for locating and penetrating into a target vessel or other target location, either from a host vessel or another starting location.

SUMMARY OF THE INVENTION

Applicants have determined that, in at least some of the procedures in which a penetration tract is formed between a host vessel (e.g., an artery such as a coronary artery) or starting location (e.g., body cavity or external location) and a target vessel (e.g., a coronary vein), it may be desirable to dilate at least a portion of the target vessel before advancement of the penetrator.

The present invention thus provides methods and apparatuses for temporarily dilating (i.e., distending, radially dilating, pressurizing or otherwise enlarging in transverse dimension) at least a portion of a target vessel to i) improve the imageability of the target vessel, and/or ii) decrease the distance that a penetrator must travel from a location where a penetrating catheter is positioned to the target vessel, and/or iii) allow for less precise aiming of the penetrator than would be required if the target vessel were not dilated, iv) improve the ability to advance a guidewire though the lumen of the target vessel and/or v) stiffen the wall of the target vessel to facilitate puncture thereof.

The dilation of the target vessel may be carried out by occluding flow through the vessel so as to cause an increase of pressure within the target vessel, or a target region within the vessel, and resultant dilation of the vessel. Alternatively, in areas where the blood pressure may be inadequate to cause the desired dilation of the target vessel, dilation may be caused by placing occluders in the vessel upstream and downstream of the region desired to be dilated and then infusing a fluid into the vessel between the occluders to thereby cause dilation of the vessel in the region between the occluders. Alternatively, the desired dilation of the target vessel may be carried out by placing a dilation member within the lumen of the vessel in the region into which the penetration is to be made and subsequently enlarging the dilation member so as to cause dilation (e.g., distension, bulging or stretching) of the wall of the vessel.

In accordance with the invention, there are provided vessel dilation catheters that incorporate one or more balloons, enlargeable members or other vessel dilating apparatus to cause the desired dilation of a target vessel. Also provided are systems that incorporate a vessel dilation catheter of the foregoing character in combination with tissue penetration catheters and ancillary equipment (e.g., guidewires, penetration tract enlarging apparatus, imaging apparatus, etc.) to create penetration tracts, fistulas, or flow channels between a starting location and a target vessel.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 3a is an enlarged partial longitudinal sectional view showing a distal portion of the tissue penetrating catheter of FIG. 2.

FIG. 3a' is an enlarged, cut-away view of a wire braid formed within the distal portion of the catheter of FIG. 2.

FIG. 3a" is a diagram of a catheter braid illustrating the braid angle and pick count of the braid of the tissue penetrating catheter shown in FIG. 2.

FIGS. 3c, 3d and 3e are transverse cross sectional views taken generally along lines 3c—3c, 3d—3d, and 3e—3e of FIG. 3a, respectively.

FIG. 3f is a perspective view of the marker structure of the tissue penetrating catheter embodiment shown in FIG. 3a.

FIG. 3g is a transverse cross sectional view through FIG. 3g—3g of FIG. 3a.

FIGS. 4a and 4a' are schematic diagrams of annular phased array transducers that may be mounted within catheters of the present invention.

FIG. 4b is a schematic diagram of an alternative single element transducer that is rotatable within or in conjunction with the catheter.

FIGS. 5a' and 5b' show the display screen of an imaging apparatus as in FIGS. 5a and 5b, and illustrate the manner in which a penetrating catheter can be rotationally oriented within a host vessel to cause a penetrator-path-indicating element (and hence the penetrator) to be aimed at a target vessel to which the penetrator is intended to travel after the target vessel has been dilated in accordance with the present invention.

FIGS. 5c' and 5d' show the display screen of an imaging apparatus as in FIGS. 4a and 4b, and illustrate the manner in which the line can be used to facilitate rotational orientation of the catheter within the host blood vessel such that the penetrator-path-indicating transducer element (and hence the penetrator) is aimed at a target vessel that has been dilated in accordance with the present invention.

FIGS. 5e and 5f illustrate the manner, in accordance with the prior art, in which the visually distinct image of the penetrator-path-indicating transducer can be used to facilitate rotational orientation of the catheter within the host blood vessel such that the penetrator-path-indicating transducer element (and hence the penetrator) is aimed at a target vessel (e.g., a vein) that has a relatively small, non-dilated diameter, or conversely, the path region incorporates the non-dilated target vessel within its scope.

FIGS. 5e' and 5f' show the display screen of an imaging apparatus as in FIGS. 5e and 5f, and illustrate the manner in which the visually distinct image of the penetrator-path-indicating transducer can be used to facilitate rotational orientation of the catheter within the host blood vessel such that the penetrator-path-indicating transducer element (and hence the penetrator) is aimed at a target vessel that has been dilated in accordance with the present invention, or conversely, the path region incorporates the dilated target vessel within its scope.

FIGS. 6a and 6b are views similar to FIGS. 5a and 5b respectively illustrating the manner, in accordance with the prior art, that the catheter embodiment of FIG. 3a can be rotationally oriented within the host blood vessel to cause the image created by the penetrator-path-indicating member of the marker structure (e.g., the particular strut member of the marker structure that is aligned with the path that will be followed by the tissue penetrator when the penetrator is advanced from the catheter body) to be aimed at a target vessel that has a relatively small, non-dilated diameter.

FIGS. 6a' and 6b' are views similar to FIGS. 5a' and 5b' illustrating how the catheter embodiment of FIG. 3a can be rotationally oriented within the blood vessel to cause the image created by the penetrator-path-indicating member of the marker structure to be aimed at a target vessel that has been dilated in accordance with the present invention.

FIG. 9 is a side elevational view of a subselective sheath having an occluder balloon formed thereon in its deflated state and accompanying introducer that are useable in combination with a tissue-penetrating catheter in accordance with the present invention.

FIG. 9a is a side elevational view of a dilator that is insertable through and useable in conjunction with the subselective sheath of FIG. 9.

FIG. 10 is a partial longitudinal sectional view of a distal portion of the subselective sheath of FIG. 9 having the dilator of FIG. 9a operatively inserted therein.

FIG. 10a is an enlarged, cross sectional view through line 10a—10a of FIG. 10.

FIG. 11 is an enlarged, longitudinal sectional view of the encircled distal portion of the subselective sheath of FIG. 9 showing the occluder balloon in its deflated state (inflated state shown in dotted lines).

FIG. 12 is a partial longitudinal sectional view of the distal portion of a double balloon vessel segment expander device of the present invention.

FIG. 12a is a schematic diagram of a portion of a human body showing the device of FIG. 12 in operation therein.

DETAILED DESCRIPTION OF PREFERRED EMBODIMENTS

Set forth herebelow are detailed descriptions of certain embodiments and examples of the catheter devices and methods of the present invention.

A. Tissue Penetrating Catheter

Figure 1:
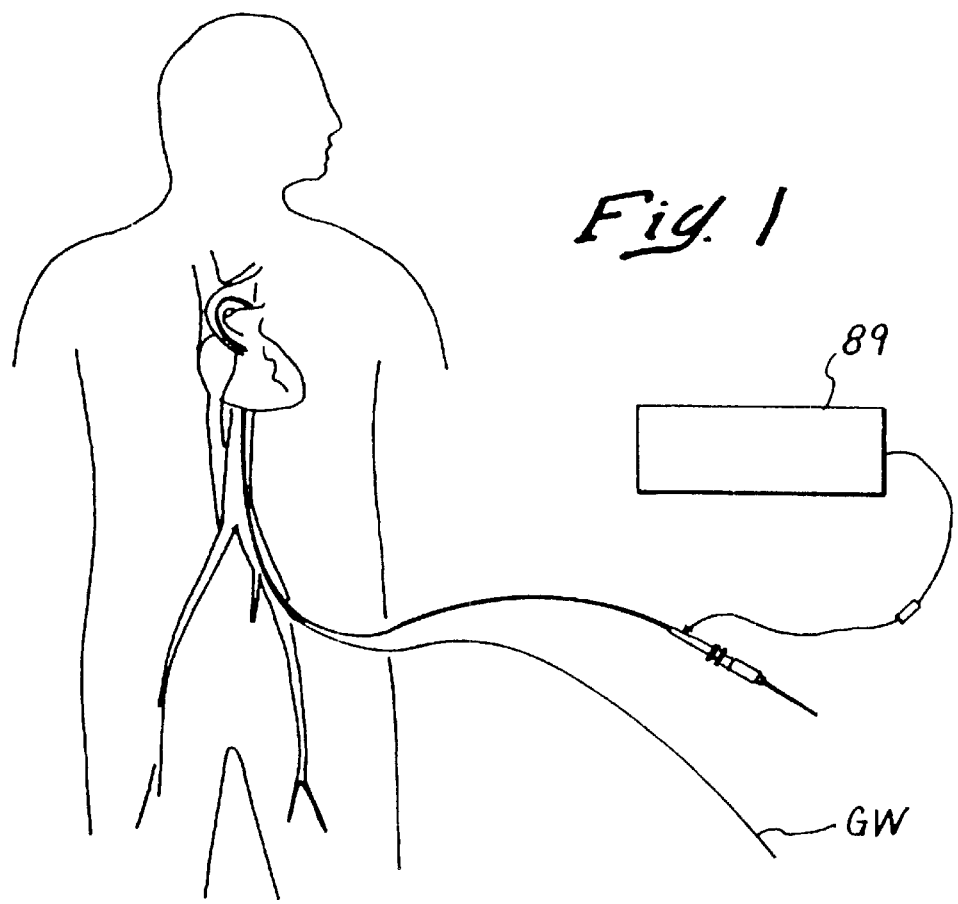
FIG. 1 is schematic illustration showing the positioning of various catheters and other apparatus during the creation of a coronary artery-to-vein flow tract in accordance with this invention.
Figure 2:
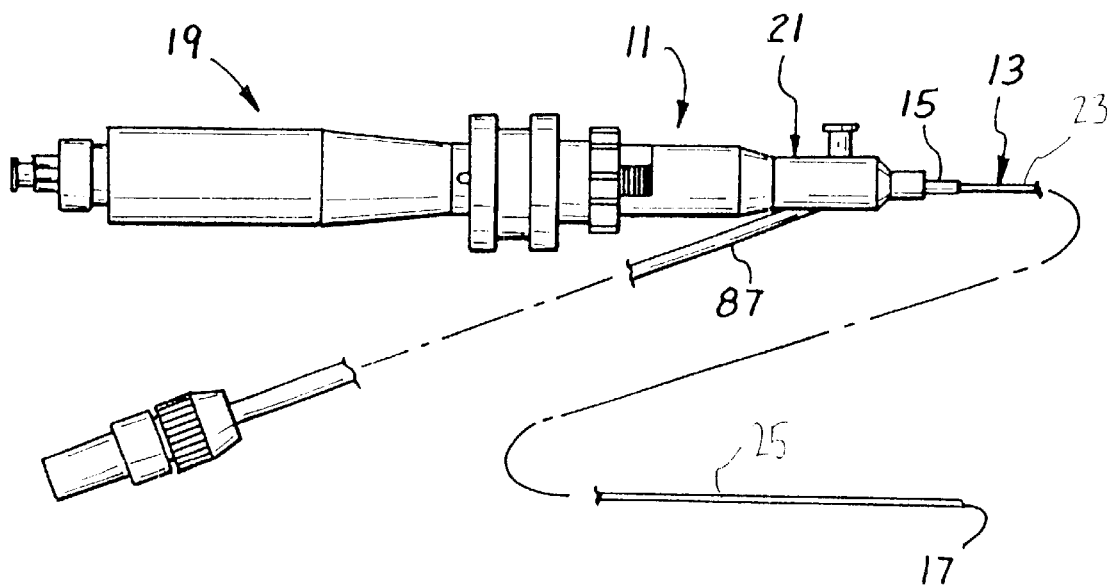
FIG. 2 is an elevational view of a tissue penetrating catheter useable to form an artery-to-vein penetration in accordance with the present invention.

FIG. 2 shows an example of one type of tissue penetrating catheter 11 that may be used to form the initial penetration from a host vessel into a target vessel that has been caused to dilate or to enlarge, in accordance with this invention, while FIG. 1 shows this particular type of catheter 11 in use on a human patient. It is to be appreciated, however, that several other types of tissue penetrating catheters may alternatively be used to form the penetration tract between host vessel and target vessel, including those described in copending U.S. patent application Ser. No. 09/505,149 entitled Sterility Barriers for Insertion of Non-Sterile Apparatus Into Catheters or Other Medical Devices filed on Feb. 15, 2000, U.S. Pat. No. 5,830,222 (Makower) and in published PCT Applications WO 98/16161, WO 98/46119, WO99/49910 and WO99/49793, the entire disclosures of which are expressly incorporated herein by reference.

The particular tissue penetrating catheter 11 shown in these drawings includes an elongated catheter body 13 having a proximal end 15, a distal end 17, a handle 19 and a hub 21 coupled to the proximal end of the catheter body 15 and to the handle. The handle 19 may also serve as a controller for use in advancing and retracting the penetrating instrument, such as a tissue penetrator 85, seen in FIG. 3a and described more fully below.

The Catheter Body

The catheter body 13 includes a relatively rigid proximal section 23 shown in FIG. 3a which may be constructed, for example, of a metal hypo tube and an elongated flexible distal section or region 25 suitably joined to the proximal section. A hand piece 19 is attached to the proximal end of the proximal section 23, as shown in FIG. 2. In the preferred embodiment the hand piece 19 and proximal section 23 are approximately 100 cm in length. The flexible distal section 25 may incorporate a reinforcement member such as a wire braid 400 as shown in FIGS. 3a and 3a' and, in the preferred embodiment, is approximately 30 cm in length. The braid 400 terminates approximately 3 cm from the distal end 17.

It has been determined that material expansion and changes in the physical properties of certain materials may occur after the catheter 11 is inserted into the patient's body and warmed from room temperature to body temperature. This material expansion and changes in the physical properties of certain materials can result in variation in the tolerances and sizing of the catheter 11 (e.g. elongation or shrinking) and can thus give rise to an unwanted modification of the position of the tissue penetrating member 85. This could, in at least some cases, interfere with the precise aiming and advancement of the tissue penetrating member as desired.

FIG. 3a" illustrates the braid angle A and pick count PC of the catheter braid 400. The "pick count" PC of the braid is, as is well known in the art, a function of the braid angle A (i.e., the greater the braid angle the more picks per inch). Also, the torque transmission and stiffness of the braided distal section 25 is a function of the braid angle (i.e., a braid angle of 90 degrees provides maximum torque transfer and a braid angle of 0 degrees provides minimum torque transfer). Typically, cardiovascular catheters used in procedures such as those described herein utilizing a venous approach have braid angles A that result in a pick count of 50–70 picks per inch. However, applicant has determined that by decreasing the braid angle A of the braid 400 within the distal section 25 of the catheter 11 to result in a lower pick count, it is possible to minimize or eliminate the unwanted longitudinal expansion of the catheter 11 and/or its components, while retaining sufficient torque transmission and acceptable stiffness to accomplish the procedures for which the catheter 11 is intended (examples of such procedures are illustrated in FIGS. 7a–8d herebelow). This variation in braid angle or picks per inch may vary depending on the material of construction of the catheter and/or the braid fiber, and the diameter of the catheter body.

Figure 3B:
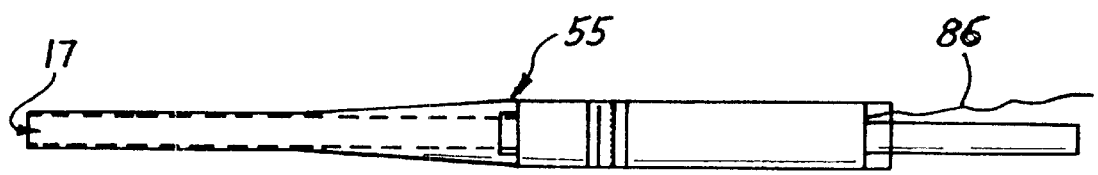
FIG. 3b is an enlarged elevational view showing the distal tip section of the tissue penetrating catheter of FIG. 2.

In instances where the catheter 11 is intended for use in a coronary vessel, at least the distal section 25 of the catheter 11 is sized to be received within either a coronary artery or a coronary vein or other lumens or body cavities of equal diameter. As seen in FIGS. 3a–3c, the catheter body section 13 has a penetrator lumen 27 that terminates distally at an exit location or exit port 29 (FIG. 3a) on a peripheral wall 31 of the catheter body. The penetrator lumen 27 extends proximally from the exit port 29 to the proximal end 15 of the catheter body 13 and communicates with the interior of the handle 19 through the hub 21. The penetrator lumen 27 contains or is adapted to receive an instrument, such as the tissue penetrator 85 shown in FIG. 3a, for penetrating out of the blood vessel in which the catheter 11 resides (i.e., the "host vessel") and to a target location. The exit port 29 is preferably located a short distance proximally of the distal end 17. A radiopaque marker (not shown) is mounted on the lumen 27 adjacent the exit port 29.

The catheter body 13 also has a guidewire lumen 35 (FIG. 3a) which extends to the distal end 17 of the catheter body 15. In this embodiment, the guidewire lumen 35 extends proximally to an inlet port 37 at the peripheral wall 31 closely adjacent the proximal section 23. The catheter body also has a lead lumen 39 (FIG. 3c) for a purpose described below.

A major section of the catheter body 13 terminates distally in a distal opening that receives a distal tip section 55 of soft, flexible, biocompatable material (FIGS. 3a and 3b). A distal portion of the distal tip section 55 extends distally to the distal end 17. The distal portion of the distal tip section 55 is of smaller cross sectional area than the adjacent region of a major section 51 to thereby define an annular shoulder 57 on the catheter body 13. The exit port 29 is spaced slightly proximally of the shoulder 57.

Phased Array Transducer

An imaging transducer 81 is fixedly mounted on the catheter 11, and in the embodiment illustrated in FIG. 3a, the imaging transducer is mounted on the distal tip section 55 just distally of the shoulder 57. In this embodiment, the imaging transducer 81 is a phased array transducer of the type shown schematically in FIG. 4a and is operative to image 360° about the catheter 11. This imaging transducer 81 comprises an annular array of individual crystals or elements 121 coupled to a multiplex circuit which is within the major section 51 of the catheter body 13 adjacent the shoulder 57, and the multiplex circuit is in turn coupled to leads 86 (FIG. 3b) which extend through the lead lumen 39 and a port 87 (FIG. 2) of the hub 21 to an imaging console 89.

When activated, the imaging transducer emits ultrasound signals and receives back echos or reflections which are representative of the nature of the surrounding environment. The imaging transducer provides an imaging signal from which an image of the surrounding structure can be created by signal processing apparatus located in the imaging console 89 and viewed on a standard display screen located near the operating table on which the patient is positioned. In a preferred practice of this invention, the phased array transducer and the accompanying circuitry and the imaging console 89 may be obtained from Endosonics of Rancho Cordova, Calif. or Intravascular Research Limited (United Kingdom).

Alternative Rotatable Transducer

In an alternate embodiment of this invention, a rotatable imaging transducer 81r of the type illustrated schematically in FIG. 4b may be used. This alternative transducer 81r comprises one (or more than one) imaging element 121r that is mounted on a rotating shaft 82 that extends through a portion of the catheter body (e.g., and out of port 39) such that it can be rotated relative to the catheter body. Alternatively, it will be appreciated that this transducer 81r may be fixedly mounted within or upon the catheter body and the entire catheter body may be rotated in order to effect rotational movement of the transducer element 121r.

Marker Structure

Figure 3F:
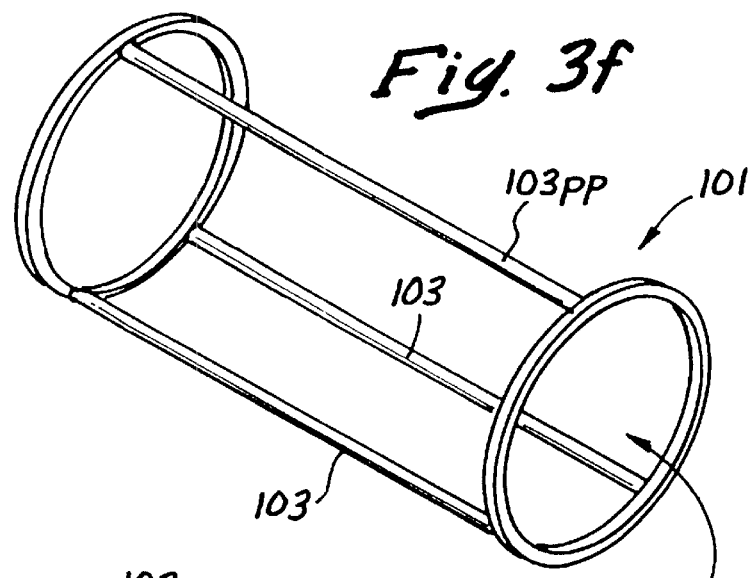
Figure 3G:
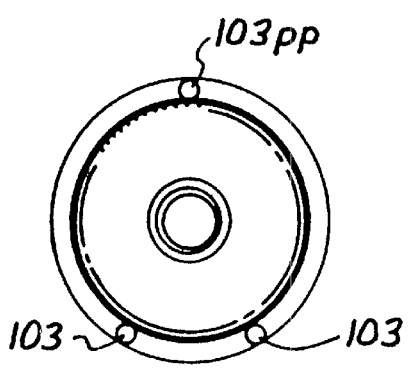

In this first embodiment (FIGS. 3a–3e), an imageable marker structure 101 is fixedly mounted on the catheter body 13 in a known circumferential orientation relative to the exit port 29. In the embodiment of FIG. 3a, the marker structure 101 is in the form of a cage (FIG. 3f and the transducer 81 is within the cage. This marker structure 101 comprises a plurality of longitudinal members 103 and 103pp disposed at circumferentially spaced apart locations about a hollow interior space 105. The hollow space 105 receives the distal tip section 55 and the transducer 81, and the transducer 81 is an onboard transducer in that it is inseparable from and not removable from the catheter body 13. In this embodiment the transducer 81 is attached to or wrapped around the catheter body 13 and permanently retained by a suitable potting composition or adhesive. As shown in FIG. 3g, one of the longitudinal members 103pp is designated as the penetrator path indicating member and is positioned at a circumferential position that is axially aligned with the exit port 29 or otherwise positioned to be indicative of the path that will be followed by the tissue penetrator 85 as it is advanced from the catheter body 13 through the exit port 29. Thus, the imageable marker structure 101 forms on the image obtainable from the imaging signal from the imaging transducer a penetrator path indication that indicates the path that will be followed by the tissue penetrator when the tissue penetrator 85 exits from the catheter.

With the construction described above, the imaging transducer 81 and the marker 101 are both mounted on the distal tip section 55 which has a smaller cross sectional area than does the adjacent region of the major section 51 of the catheter body 13. Accordingly, the cross sectional area of the catheter body 13 at the region containing the imaging transducer 81 and the marker 101 can still be relatively small. Also, the exit location 29 is closely adjacent to the imaging transducer 81 and may be, for example, about 3 mm from the imaging transducer. This minimizes the likelihood of any significant torsional displacement of the exit location 29 relative to the marker 101 and imaging transducer 89. It may also be appreciated that the imaging transducer may be mounted such that the exit port is located directly at the point at which the transducer is affixed to the catheter, eliminating any displacement.

FIGS. 6a and 6b show an image of what the operator sees on the display screen of the imaging console 89 when the catheter 11 is advanced into the host blood vessel, without the benefit of the present invention. Specifically, FIG. 6a shows an image of the catheter 11, an image 143 of the host blood vessel into which the catheter 11 has been inserted (i.e., the blood vessel in which the catheter 11 resides) and an image of a target blood vessel 145 adjacent to the blood vessel 143. In this particular illustration, the blood vessels represented by images 143 and 145 are a coronary artery and coronary vein, respectively.

In FIG. 6a, the image created by the penetrator-path-indicating member 103pp of the marker structure 101 (FIG. 3g), as represented by line or artifact 147, does not extend into the lumen of the target blood vessel 145. Thus, if the tissue penetrator 85 were to be advanced from the catheter 11 while the catheter 11 is in the rotational orientation shown in FIG. 6a, the tissue penetrator would not advance into the lumen of the target blood vessel 145, as desired. However, by rotating the catheter 11 within the host blood vessel 143, the operator may cause the image created by the penetrator-path-indicating member 103 pp of the marker structure 101, as represented by line or artifact 147, to extend into the lumen of the target blood vessel 145 as illustrated in FIG. 6b. Thus, if the tissue penetrator 85 were to be advanced from the catheter 11 while the catheter 11 is in the rotational orientation shown in FIG. 6b, the tissue penetrator 85 would advance into the lumen of the target blood vessel 145, as desired.

In contrast to the images seeing in FIGS. 6a and 6b, utilization of the techniques of the present invention results in the images seen in FIGS. 6a' and 6b'. That is, dilation of the target vessel 145' presents a larger and more well-defined target. In addition, is believed that certain techniques described herein alter the physical character of the wall of the target vessel 145' so that the image generated on the display screen is clearer. For example, when using an intravascular ultrasound (IVUS), the wall of the dilated target vessel 145' appears in greater contrast, in relation to the image of the wall of the target vessel 145 as seen in FIG. 6b when it is not dilated. One possibility is that dilation of the target vessel 145' renders the wall thereof taut, while the un-dilated wall is relatively flaccid.

Figure 4:
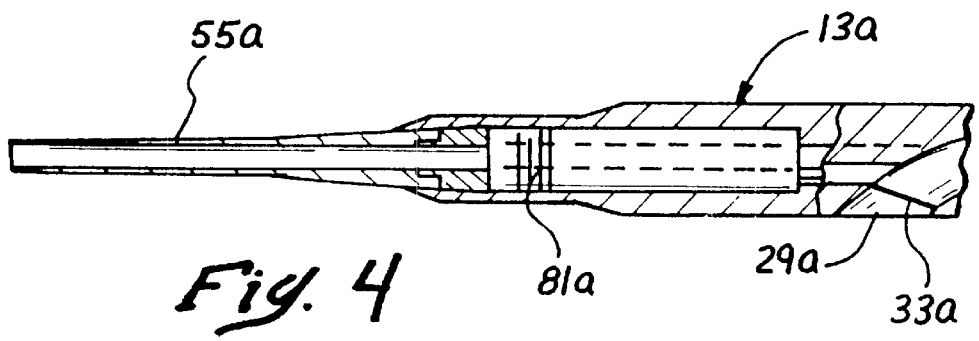
FIG. 4 is a partial longitudinal sectional view similar to FIG. 3a illustrating a second embodiment of the catheter.

FIG. 4 shows a second embodiment of the catheter 11 a which is identical to the catheter 11 in all respects not shown or specified as being different herebelow. Portions of the catheter 11a corresponding to portions of the catheter 11 are designated by corresponding reference numerals followed by the letter suffix "a".

The primary difference between the catheters 11 and 11a is that the catheter 11a has no imageable marker structure 101. Instead, its imaging transducer 81 a is mounted in a fixed position such that one particular element 121pp (or a group of particular elements) is/are designated as the penetrator path indicator(s) and is/are mounted in a fixed orientation within or upon the catheter. Thus, a selected one (or more than one but less than all) of the individual imaging elements 121 (e.g., crystals) of the phased array is/are positioned in known spacial relation to the path or plane of the path that will be followed by the tissue penetrator as it exits from the catheter, and thus are designated as the path indicator element(s) and shall be referred to herein as the "penetrator-path-indicating element 121pp." The imaging elements 121, which may be adhered to the catheter body 13a, are mounted on the catheter 11 at known circumferential locations relative to the path that will be followed by a tissue penetrator as the tissue penetrator advances from the catheter 11 through the exit port 29a. The image obtained from the imaging signal from the imaging transducer 81a is thereby useable by the operator to rotationally orient the catheter 11 such that when the tissue penetrator subsequently exits from the catheter, the tissue penetrator will extend into the target as desired. Thus, because the imaging elements 121a are mounted on the catheter body 13 in fixed relationship to the catheter body and in a known circumferential orientation relative to the exit location 29a, the imaging transducer 81a can be used to provide an imaging signal for use in locating an adjacent blood vessel or other structure and identifying the angular orientation of the exit location. If desired, the imaging elements of the imaging transducer 81 of the catheter 11 can be oriented in the same fashion as described above for the catheter 11a. In this event, the only difference between the catheters 11 and 11a would be that the catheter 11 has an imaging marker 101 and the catheter 11a does not.

Figure 5A:
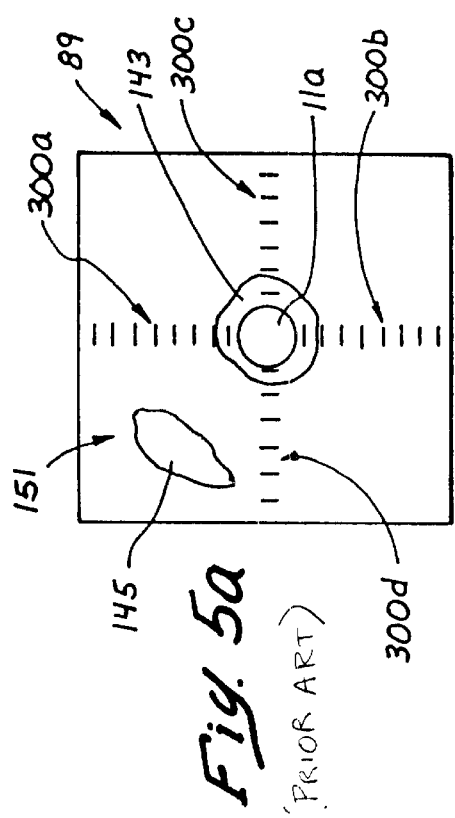
FIGS. 5a and 5b show the display screen of an imaging apparatus showing standard quadrant-indicating hash marks on the screen, and illustrate the manner, in accordance with the prior art, in which a penetrating catheter can be rotationally oriented within a host vessel to cause a penetrator-path-indicating element on catheter (and hence the penetrator) to be aimed at a target vessel of relatively small, non-dilated diameter, to which the penetrator is intended to travel.

FIG. 5a shows an image 151 of the catheter 11a (FIG. 4) in the host blood vessel 143 in which that catheter is positioned, as well as an image of the target location 145, shown here as another blood vessel, without the benefit of the present invention. Standard serial hash marks 300a, 300b, 300c and 300d are formed on the imaging screen as shown, generally dividing the screen into four quadrants. In this instance, the transducer 81b is fixedly mounted within the catheter 11a such that its penetrator path indicating transducer element 121pp is in the 12 o'clock position and aligned with the top array of hash marks 300a on the imaging screen. Thus, the top array of hash marks 300a serve as a visual indicator of the path that will be followed by the tissue penetrator 85 as it is advanced from the catheter 11a. In the showing of FIG. 5a, one can see that the top hash marks 300a do not enter the target location 145 and thus, it can be concluded from this image that the tissue penetrator 85 is not properly aimed at the target location. However, by rotating the catheter 11a in the host blood vessel 143, to the position shown in FIG. 5b, the top array of hash marks 300a is caused to pass directly through the target location 145, thus indicating to the operator that the tissue penetrator 85 can now be advanced from the exit port 29a to properly penetrate from the host vessel 143 into the target location 145, as desired.

Figure 5B:
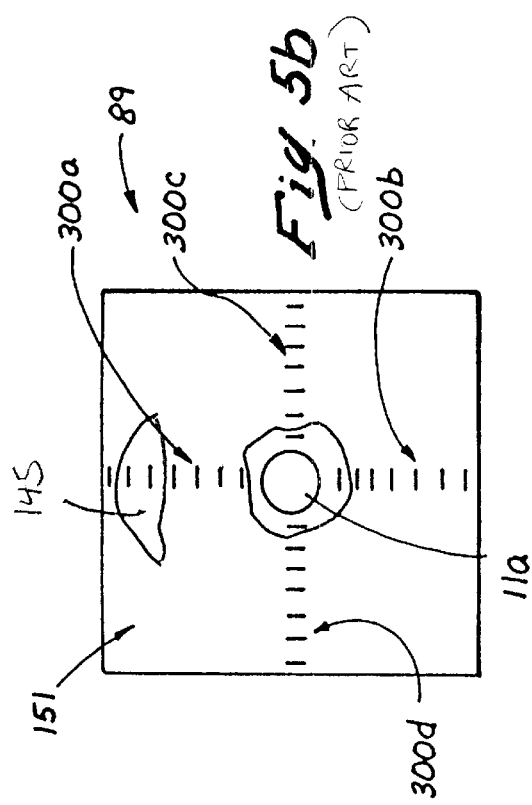
Figure 5A:
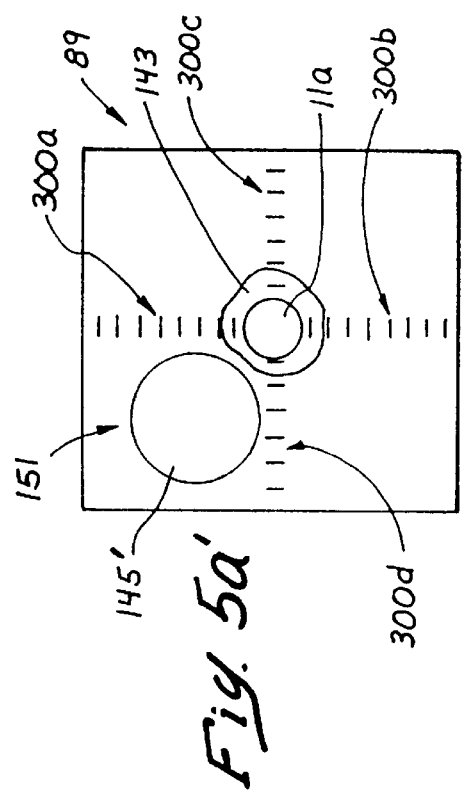
Figure 5B:
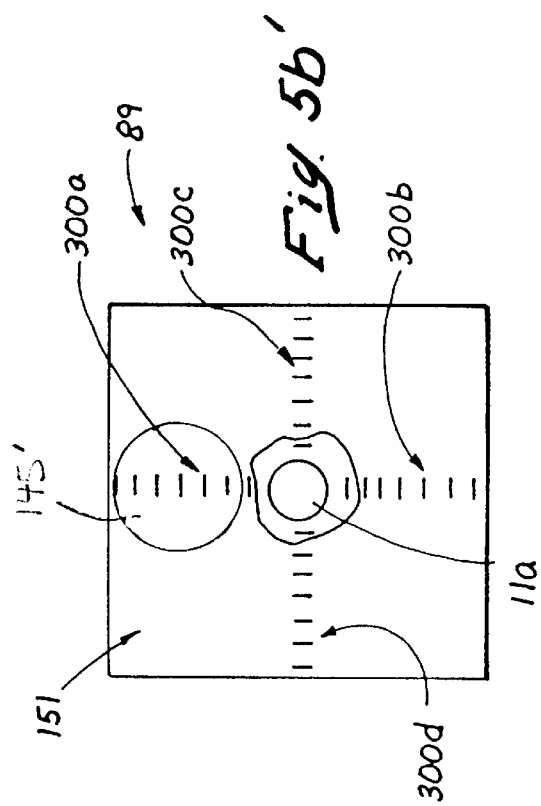

Again, in contrast to the images seeing in FIGS. 5a and 5b, utilization of the techniques of the present invention results in the images seen in FIGS. 5a' and 5b'. That is, dilation of the target vessel 145' presents a larger and more well-defined target. Therefore, the circular image of the dilated target vessel 145' crosses the serial hash marks 300a sooner and remains there longer.

Figure 5C:
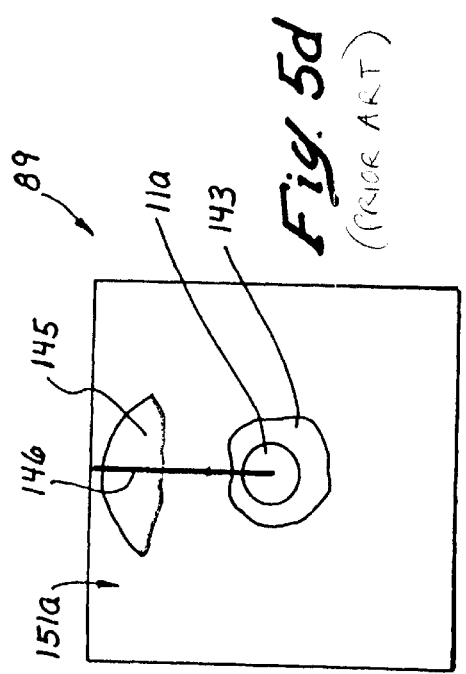
FIGS. 5c and 5d show the display screen of an imaging apparatus whereon a line has been marked to denote the location of the particular penetrator-path-indicating element of the fixed-transducer catheter of FIG. 4, and illustrate the manner, in accordance with the prior art, in which the line can be used to facilitate rotational orientation of the catheter within the host blood vessel such that the penetrator-path-indicating transducer element (and hence the penetrator) is aimed at a target vessel that has a relatively small, non-dilated diameter.
Figure 5D:
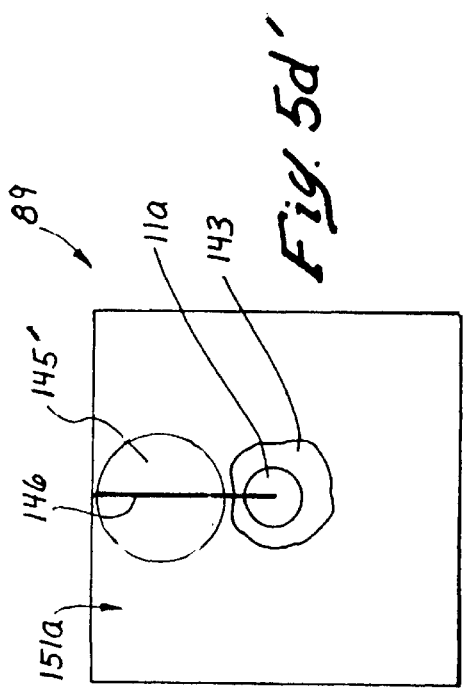
Figure 5C:
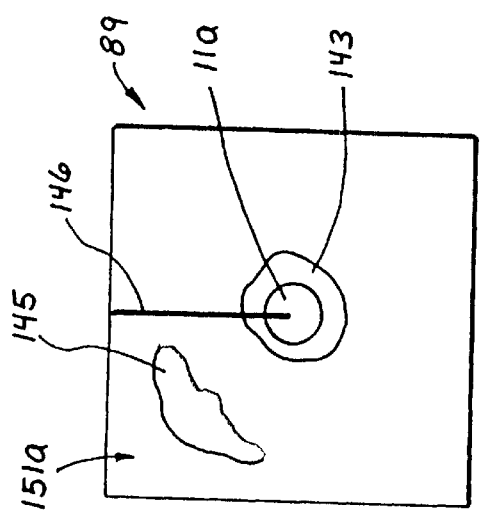
Figure 5D:
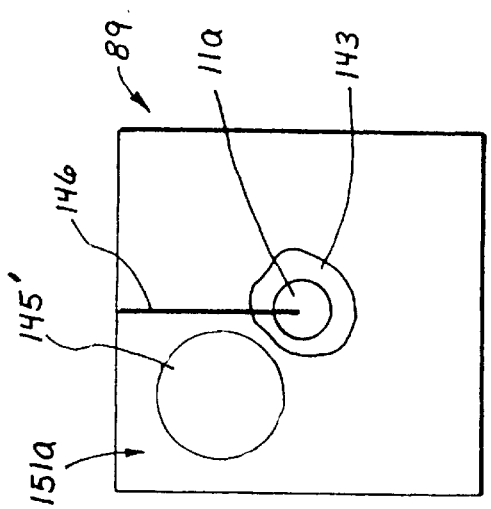

FIGS. 5c and 5d show an image 151a of the catheter 11a (FIG. 4) in the host blood vessel 143 in which that catheter is positioned, as well as an image of the target location 145, shown here as another blood vessel, again without the benefit of the present invention. A vertical line 146 has been created on the screen 146 in alignment with the position of a penetrator path indicating transducer element 121pp of the phased array transducer 81b. Thus, the line 146 serves as a visual indicator of the path that will be followed by the tissue penetrator 85 as it is advanced from the catheter 11a. It will be appreciated by those of skill in the art that this line 146 may be created on the imaging screen 89 electronically (e.g., as an illuminated or colored line on the image) or it may be physically marked on the screen 89 (e.g., by felt-tipped marker, ink, or other suitable marking material or apparatus such as a template). In the depiction of FIG. 5c, one can see that the line 146 does not enter the target location 145 and, thus, it can be concluded form this image that the tissue penetrator 85 is not properly aimed at the target location 145. However, by rotating the catheter 11a in the host blood vessel 143, to the position shown in FIG. 5d, the line 146 is caused to pass directly through the target location 145, thus indicating to the operator that the tissue penetrator 85 can now be advanced from the exit port 29a to properly penetrate from the host vessel 143 into the target location 145, as desired.

Utilization of the techniques of the present invention, in contrast, results in the images seen in FIGS. 5c' and 5d'. That is, dilation of the target vessel 145' presents a larger and more well-defined target. Therefore, the circular image of the dilated target vessel 145' crosses the vertical line 146 sooner and remains there longer. In addition, FIG. 5d' illustrates the close spacing between the wall of target vessel 145' and catheter 11a. Because of this reduced spacing upon dilation of the target vessel 145', the distance that the penetration element 85 of the catheter 11a must travel before entering the target vessel is reduced. Furthermore, dilation of the target vessel 145' facilitates penetration of the element 85 through the wall of the target vessel, because the wall is relatively more taut than in the flaccid, un-dilated condition shown in FIG. 5d.

Figure 5E:
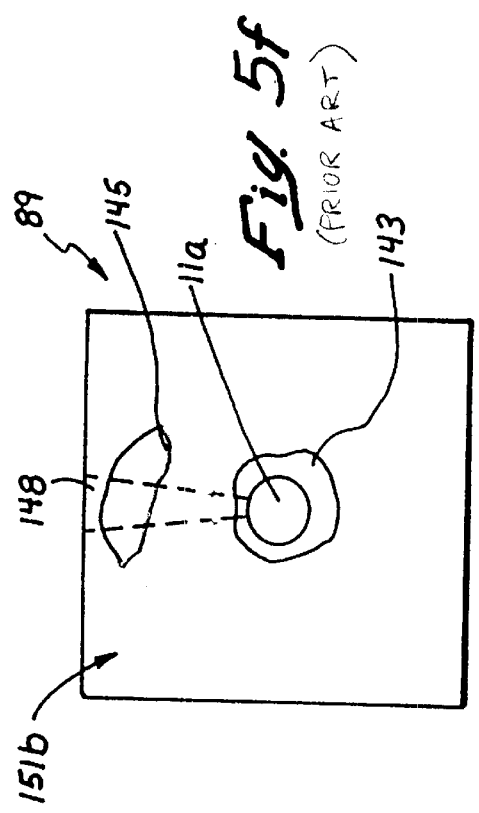
FIGS. 5e and 5f show the display screen of an imaging apparatus on a fixed-transducer catheter as in FIG. 4 wherein the penetrator-path-indicating element(s) of the imaging transducer is/are electronically modified to produce an image that is i) visually distinct from the images produced by the other elements of the transducer array, or ii) modified to produce multiple lines that define a path region. These
Figure 5E:
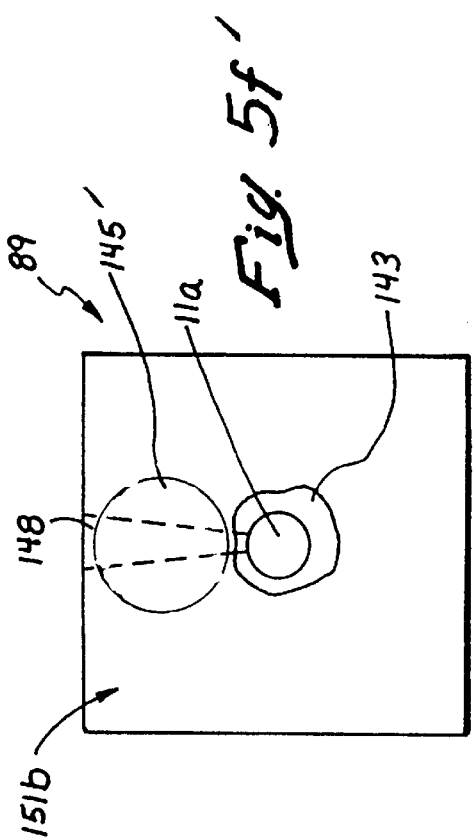
Figure 5F:
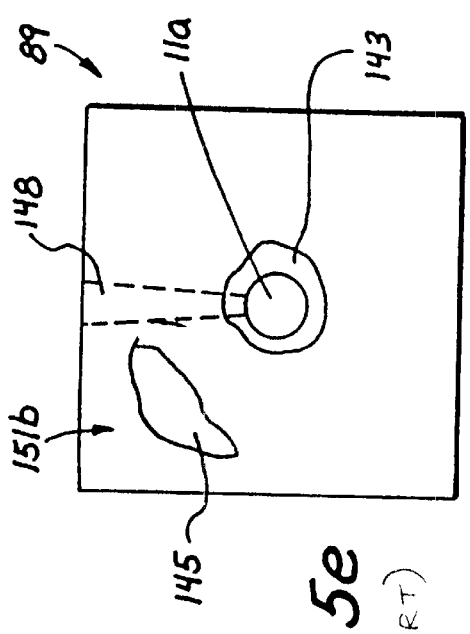
Figure 5F:
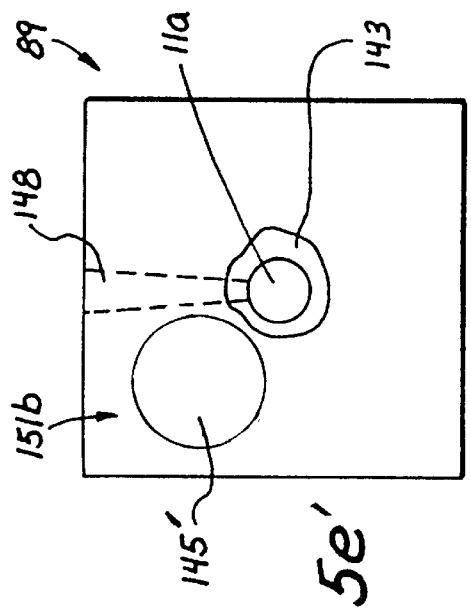

FIGS. 5e and 5f show an image 151b of the catheter 11a (FIG. 4) in the host blood vessel 143 in which that catheter is positioned, as well as an image of the target location 145, shown here as another blood vessel, once again without the benefit of the present invention. The penetrator path indicating element 121pp of the phased array transducer 81b has, in this case, been modified to provide an image that is enhanced or otherwise visually discernible from the images produced by the other transducer elements 121b of the array.

In this manner, a penetrator path region 148 is visible on the screen 89 in the region that is imaged by the penetrator path indicating element 121*pp*. Thus, the penetrator path region 148 serves as a visual indicator of the path that will be followed by the tissue penetrator 85 as it is advanced from the catheter 11*a*. It will be appreciated by those of skill in the art that this penetrator path region 148 may be created by causing the penetrator path transducer element 121*pp* to receive more power than the other transducer elements 121*b* or by otherwise modifying or processing the signal received from that penetrator path indicating transducer element 121*pp*. In the showing of FIG. 5*e*, one can see that the target 145 is not encompassed by the penetrator path region 148 and, thus, it can be concluded from this image that the tissue penetrator 85 is not within acceptable range of the target location 145. However, by rotating the catheter 11*a* in the host blood vessel 143, to the position shown in FIG. 5*f*, the target 145 is brought within an appropriate range of the penetrator path region 148, thus indicating to the operator that the tissue penetrator 85 can now be advanced from the exit port 29*a* to properly penetrate from the host vessel 143 into the target location 145, as desired. Additionally, it is to be understood that the penetrator path indicating transducer element 121*pp* or the output on the imaging console may be additionally modified to allow imaging or project images of only that region within a predetermined distance (e,g,, up to 3 mm) of the host vessel 143 thereby signalling to the operator the possible target locations that are out of the intended range of the tissue penetrator 85 or subsequent systems or devices that may be employed to complete the intended procedure.

The images seen in FIGS. 5*e*' and 5*f*' are similar to those in FIGS. 5*e* and 5*f*, but reflected dilation of the target vessel 145'. As result, the target vessel 145' presents a larger and more well-defined target and the circular image of the dilated target vessel crosses the penetrator path region 148 sooner and remains there longer. Further, as mentioned above, the wall of the target vessel 145' is more closely spaced to the catheter 11*a* and is relatively easier to puncture.

As an alternative to creating a penetrator path region by increasing the power transmitted to the penetrator path element transducer(s), it will be appreciated that this region 148 may be created on the imaging screen 89 electronically (e.g., as an illuminated or colored sector on the image) or it may be physically marked on the screen 89 (e.g., by felt tipped marker or other suitable marking material or apparatus such as a template). In addition, the penetrator path region may be defined by the enhancement (e.g. electronic illumination, marker or template) of two lines such as that depicted by line 146, modified to define boundaries to the region 148 within which is defined an acceptable range of penetration zone.

It will be appreciated that the electronically enhanced penetrator path indicating transducer 121pp may be used in conjunction with the hash marks 300*a*, 300*b*, 300*c*, and 300*d* shown in FIGS. 5*a*'–5*b*' and/or the line 146 shown in FIGS. 5*c*' and 5*d*', thereby enabling the operator to utilize multiple indicia to determine the appropriateness of the size and distance range of the target location 145 before advancing the tissue penetrator 85. In this way, the operator is provided with a range of acceptable accuracy depending on the desired result and taking into account what procedures may be performed subsequently (i.e. placement of a connection device or other catheter devices).

B. Apparatus Useable for Causing Dilation of a Vein or Other Vessel to Facilitate Imaging and/or Penetration of a Target Vessel Any suitable means for dilating (e.g., distending, radially enlarging, pressurizing stretching, bulging, or otherwise enlarging the transverse cross-sectional dimension) a vessel or associated structure (e.g., the coronary venous sinus) may be used to carry out the dilation of the target vessel in accordance with this invention. For example, manual pressure or a tourniquet may be applied in some cases, such as where the vessel or associated structure to be occluded is located in an arm, leg or superficially in the patient's body. Alternatively, any suitable type of lumen-occluding catheter (e.g., a balloon catheter) may be inserted into the vasculature associated with the target vessel and used to cause the desired temporary dilation of the target vessel. Or, alternatively, an enlargeable member may be positioned in the lumen of the target vessel and caused to enlarge, thereby causing the wall of the target vessel to become dilated in the target region wherein the penetration is to be made.

Examples of commonly available balloon catheters that could be used for occlusion of a vessel or associated structure to cause an increase in pressure within the target vessel and resultant dilation of the vessel include but are not limited to PTCA balloon catheters (e.g., Ninja™ PTCA catheter available from Cordis, Inc., Warren, N.J.), Swan-Ganz Catheters (e.g., #111F7 available from Baxter Healthcare Corporation, Critical Care Division, Irvine, Calif.) or simple venous guide, angiography or infusion catheters that have balloons near their distal ends (e.g., Vuepor™ venous guide catheter available from Cardima, Inc. of Freemont, Calif.).

Alternatively, more specialized types of vessel dilation catheters may be used in accordance with this invention. For example, FIGS. 9–15*a* show examples of specialized vessel dilation catheters 400, 500, 600, 700 and 800 that are useable to fully or partially dilate a target vessel in accordance with this invention. Some of these vessel dilating catheters incorporate balloons or occluders for fully or partially blocking blood flow through the associated vasculature to cause dilation of at least the portion of the target vessel and into which the penetrator 85 will pass, prior to and/or during the passage thereof from a tissue penetrating catheter 11, 11*a* located in an adjacent host vessel into the target vessel. For example, if the target vessel is a target vein, blood flow through the lumen of the target vein, or the lumen of another vein into which the target vein drains, or a venous sinus into which the target vein drains (such as the coronary venous sinus), may be blocked by the vessel dilating catheter.

Specifically, FIG. 9 illustrates a subselective sheath 400 which can be used in accordance with the principles of the present invention to dilate a target vessel. The subselective sheath 400 includes a sheath body 402 have a proximal hub 404, and a balloon 405 on a distal end. The distal end of the sheath 400 is seen enlarged in FIG. 11, which further illustrates the balloon 405' in its expanded state. The sheath 400 further includes a lumen 406, and may include radiopaque structure 408 thereon in the vicinity of the balloon 405.

Introduction of the subselective sheath 400 into a vessel is typically accomplished with the help of a guidewire GW as seen in FIG. 10*a* sized to pass through a lumen 409 of an obturator 411. The obturator 411 is seen in FIG. 9*a* and is sized to fit closely through the lumen 406 of the subselective sheath 400. The assembly of the subselective sheath 400, obturator 411, and guidewire GW, is seen in longitudinal section in FIG. 10, and in transverse section in FIG. 10a. The obturator 411 terminates in a tapered tip 411d that facilitates passage of the obturator 411 and the subselective sheath 400, through a puncture hole in a vessel of the patient. More particularly, the guidewire GW is first introduced into the vessel, and then the combination of the subselective sheath 400 and obturator 411 is advanced over the guidewire, with the tapered tip 411d and a small taper 410 on the subselective sheath body 402 facilitating passage of the larger diameter elements into the vessel.

FIG. 12 illustrates another catheter device 500 for dilating a target vessel in accordance with the present invention that utilizes a pair of spaced apart inflatable balloons. In particular, the device 500 comprises a catheter body 502 having a guidewire lumen 504 extending therethrough to a distal tip 506. A proximal balloon 508 and a distal balloon 510 are affixed to the catheter body 502 and spaced apart a predetermined distance. The proximal balloon 508 and the distal balloon 510 may be supplied with inflation fluid through separate lumens, or through a common lumen 512 as shown. The balloons 508, 510 are sized to occlude the particular vessel in which the catheter device 500 will be used.

The two inflation balloons 508 and 510 are desirably positioned close to the distal tip 506 of the catheter body 502, and are spaced apart varying distances in accordance with different methods of dilating a target vessel, as will be explained.

FIG. 12a schematically illustrates usage of the catheter device 500 to dilate a target vessel 520 within a forearm 522 of a patient. In an adjacent vessel 524, a penetration catheter 526, such as a catheter as previously described herein, is shown in operation with a tissue penetrating element 528 extending into the target vessel 520. More specifically, the penetrating element 528 passes through a wall of the host vessel 524, through any tissue between the two vessels, through the wall of the target vessel 520, and into the lumen of the target vessel. Because of the dilation of the target vessel 520 caused by the catheter device 500, imaging of the target vessel is improved because of its increased size and/or because (in cases where the imaging is by ultrasound) the wall of the target vessel is rendered more ultrasound reflective due to increased echogenicity. In addition, aiming of the penetrator 528 at the target vessel is easier not only because of the enhanced image of the target vessel, but also because the target vessel is larger and easier to hit and/or because the distance between the penetrating catheter 500 and the target vessel is decreased due to the enlargement of the target vessel. Also, penetration of the target vessel 520 by the penetrating element 528 is facilitated because the wall of the target vessel is made more taut by the dilation.

Dilation of the target vessel 520 may be accomplished in different ways utilizing the catheter device 500. In its most simple form, the catheter device 500 physically enlarges a target region 530 of the target vessel 520 upon inflation of the balloons 508, 510. That is, the balloons 508, 510 are spaced apart a short enough distance to place the wall of the target vessel 520 in the target region 530 in axial tension, and hold it there in a dilated state. The maximum spacing between the balloons 508, 510 to insure such tension and dilation varies depending on the lumen diameter, elasticity of the wall of the target vessel, how much the balloons 508, 510 are inflated, etc. In one specifically contemplated embodiment, the maximum spacing between the two balloons 508, 510 to insure dilation of a target region of a target vessel their between is about 2 cm, more preferably about 1 cm.

In an alternative embodiment, the catheter device 500 may be provided with an infusion lumen 540, shown in FIG. 12 having an aperture 542 opening between the balloons 508, 510. In such an embodiment, fluid may be infused through the aperture 542 into the lumen of the target vessel 520 after inflation of the balloons 508, 510. Introduction of the fluid infusate will pressurize the target region 530 of the target vessel 520, thus causing the desired dilation. Again, dilation of the target region 530 enables easier imaging and penetration of the target vessel 520 by the penetration catheter 526. Of course, because the fluid will pressurize and dilate the target vessel wall, the spacing between the balloons 508, 510 is not as important as in the previously described embodiment, but a maximum spacing of about 10 cm is preferred. Various infusion fluids may be used to pressurize the target vessel 520, such as, for example, saline or radiographic contrast fluid. It should also be understood that term "fluid" in this context means both liquids and suitable gases.

Optionally, a perfusion bypass lumen 550 may be provided in the catheter device 500 to permit continued blood flow through the target vessel 520 after the balloons 508, 510 have been inflated. In addition, an imageable marker 552 such as a marker that is radiopaque or visible on ultrasound, may be formed within or on the catheter body 502 between the balloons 508, 510. Because of the presence of the marker 552, imaging and penetration of the target region 530 between the balloons 508, 510 by the penetration catheter 526 is further facilitated.

It should be noted at this point that dilation of the target vessel 520 by fluid pressurization may provide an additional benefit; that of placing hoop stresses on the wall of the target vessel. It is believed that the expansion of the target vessel 520 by internal pressurization causes the vessel wall to better reflect certain types of imaging waves. For example, the image on the display screen of an intravascular ultrasound (IVUS) imaging device of an internally pressurized vessel is somewhat more clear and distinct than that of a similarly sized unpressurized vessel. One possible explanation is that the vessel wall is placed in tension by the internal pressurization, and thus becomes more elastic, which more effectively reflects sound waves, somewhat like tightening a drum head.

Figure 13:
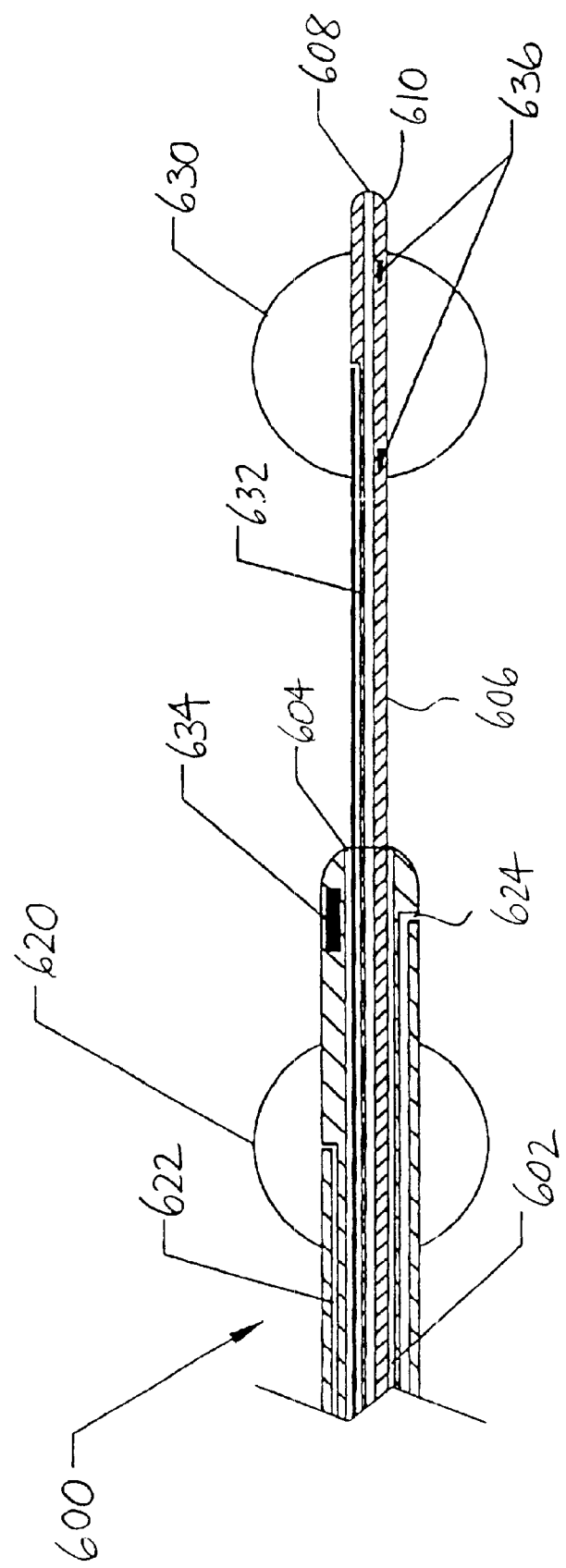
FIG. 13 is a partial longitudinal sectional view of a modified subselective sheath having an occluder balloon formed thereon and a second balloon catheter that has been passed through the subselective sheath to accomplish a two-balloon vessel segment dilation in accordance with the present invention.

FIG. 13 illustrates a catheter system 600 of the present invention that utilizes two catheter bodies or elongate devices 602, 606 to dilate a target vessel using two spaced apart balloons. More specifically, the catheter device 600 includes an outer catheter body 602 having a guide lumen 604 for receiving an inner catheter body 606. The inner catheter body 606 is sized to slide within the guide lumen 604 and includes a guidewire lumen 608 extending therethrough to a distal tip 610. In this regard, the outer catheter body 602 may be initially advanced through a target vessel, with the inner catheter body 606 being positioned within the guide lumen 604 during advancement, or inserted later through the guide lumen from the proximal end of the outer catheter body. The catheter device 600 is thus a two-stage device, wherein the outer catheter body 602 may be utilized by itself as explained above with respect to the catheter shown in FIG. 9, and the inner catheter body 606 used only if necessary.

The outer catheter body 602 has an inflation balloon 620 mounted thereon near the distal end and supplied with inflation fluid through an inflation lumen 622. A fluid infusion lumen 624 whose function will be described below is also provided on the outer catheter body 602. Likewise, the inner catheter body 606 has an inflation balloon 630 mounted thereon near the distal tip 610 and supplied with inflation fluid through a lumen 632. Various imageable markers, such as the marker 634 on the outer catheter body 602 and 636 on the inner catheter body 606, may be provided to indicate the location of the catheter bodies and/or balloons.

In use, as mentioned above, the outer catheter body 602 alone, or in conjunction with the inner catheter body 606, is transluminally advanced into a target vessel. Inflation balloon 620 occludes the target vessel which, if it is a vein, causes blood to back up behind the balloon and pressurize a target region of the target vein. Subsequently, an imaging apparatus on a penetration catheter or elsewhere can be used more easily and efficiently to locate, aim at and/or penetrate into, the target vein.

Alternatively, or if the venous blood pressure with the target vein is insufficient to dilate the vein, the inner catheter body 606 may be deployed so that the balloon 630 thereon is spaced a predetermined distance from the balloon 620 on the outer catheter body 602. Subsequently, as mentioned above with respect to the catheter device 500 of FIG. 12, mere inflation of the two balloons 620, 630 may be sufficient to dilate the target region of the target vessel therebetween. Alternatively, fluid may be infused through the lumen 624 to internally pressurize the target region between the two balloons. Again, dilation of the target region facilitates imaging and penetration thereof.

Figure 14:
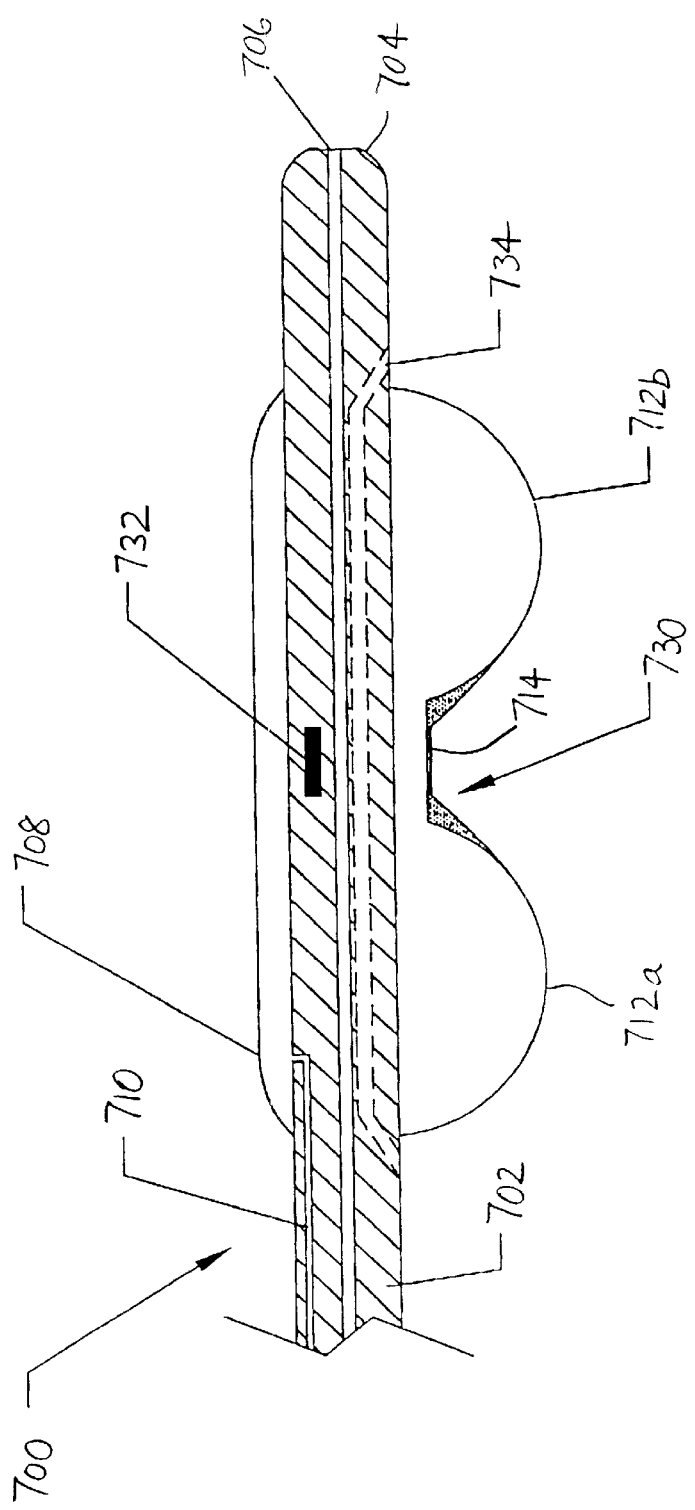
FIG. 14 is a partial longitudinal sectional view of the distal portion of a vessel expansion catheter device of the present invention having an irregularly shaped balloon for expansion of the vessel.

FIG. 14 illustrates a still further catheter device 700 of the present invention for dilating a target vessel to be imaged and accessed by a penetrating catheter. The catheter device 700 includes an elongate catheter body 702 terminating at a distal tip 704 and having a guidewire lumen 706 therethrough. An irregularly-shaped inflation balloon 708 is mounted on the catheter body 702 and is supplied with inflation fluid through a lumen 710. The inflation balloon 708 has, on at least one side, a pair of lobes 712a, 712b that extend radially outward from a relief region 714 therebetween. The lobes 712a, 712b are spaced apart a sufficient distance so that a target region of a target vessel in which the catheter device 700 is located may be dilated. That is, as with the dual-balloon embodiment of FIG. 12, the lobes 712a, 712b physically dilate the target vessel and place the wall of the vessel therebetween in axial tension.

Figure 14A:
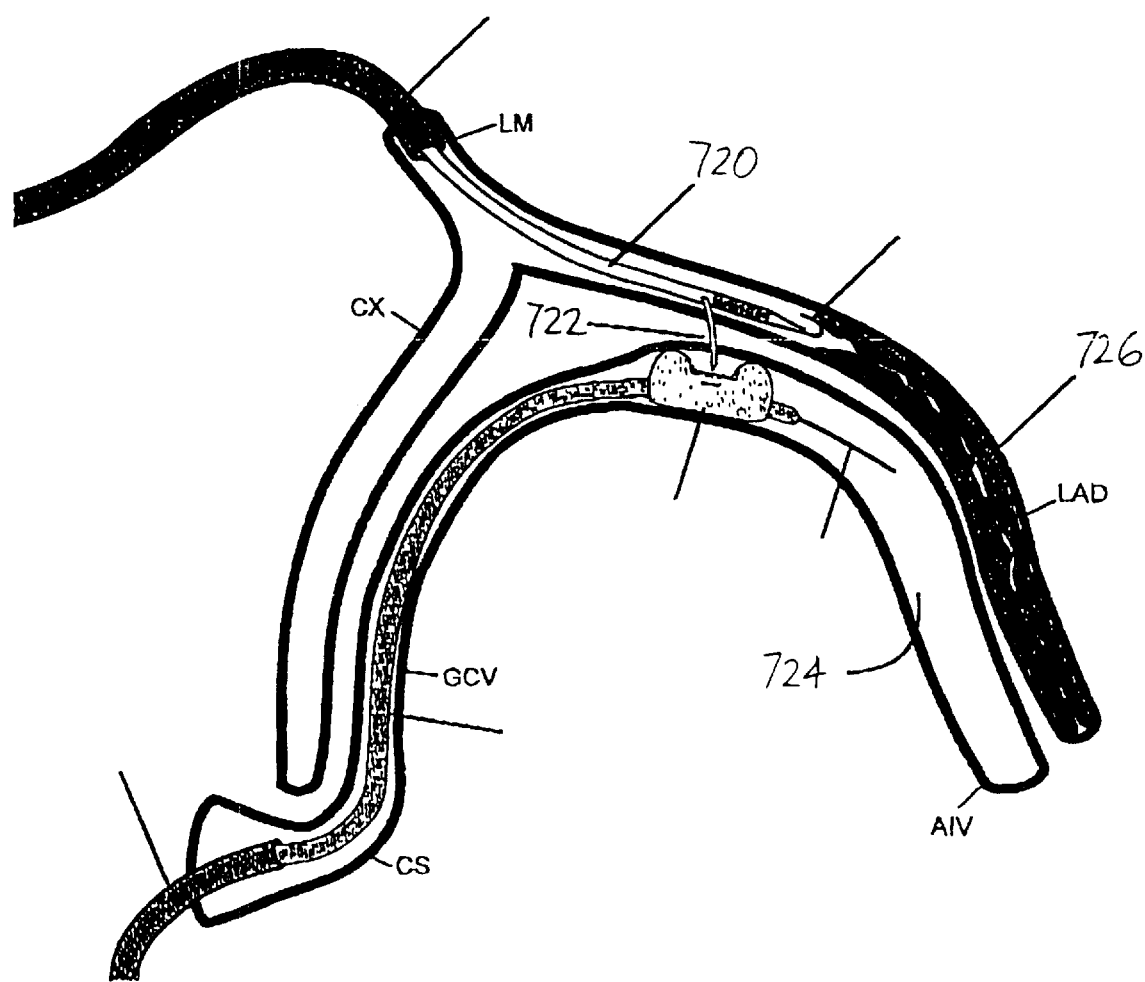
FIG. 14a is a schematic diagram of a portion of a human body showing the device of FIG. 14 in operation therein.

Usage of the catheter device 700 is shown in FIG. 14a in which a penetrating catheter 720 can more easily image the dilated target region of the target vessel 724 after placement and inflation of the balloon 708. A tissue penetrating element 722 is shown extending from the catheter 720 through the wall of the host vessel 726, intervening tissue, and wall of the target vessel 724. The recess created by the relief region 714 between the lobes 712a, 712b enables passage of the penetrating element 722 into the target vessel 724 without puncture of the balloon 708. To further help prevent puncture of the balloon 708, a reinforcement layer 730 may be provided on the relief region 714 and on the facing sides of the lobes 712a, 712b. Reinforcement layer 730 may be a metallic or other such tough coating, or may be a structure incorporated into the catheter body 702 that is impenetrable by the penetrating element 722.

An imageable marker 732 on the catheter body 702 further helps in aiming of the tissue penetrating element 722. In addition, a perfusion bypass lumen 734 may also be provided to permit blood flow through the target vessel even after the balloon 708 is inflated. Optionally, an infusion lumen (not shown) may be included in the catheter body 702 to infuse fluid (e.g., saline or radiographic contrast medium) into the space between the lobes 712a, 712b to cause further distention or bulging and/or increased tautness of the target vessel wall in that region.

Figure 15A:
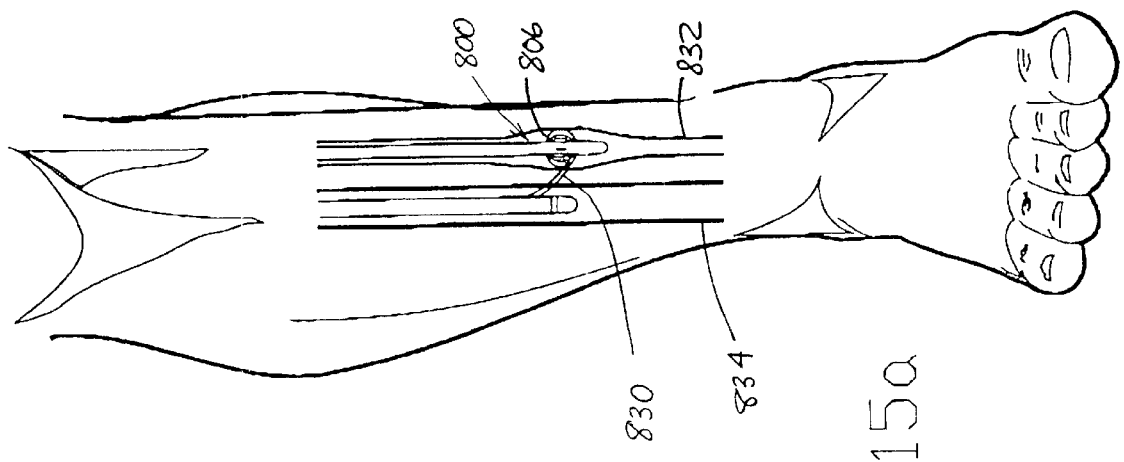
FIG. 15a is a schematic diagram of a portion of a human body showing the device of FIG. 15 in operation therein.
Figure 15:
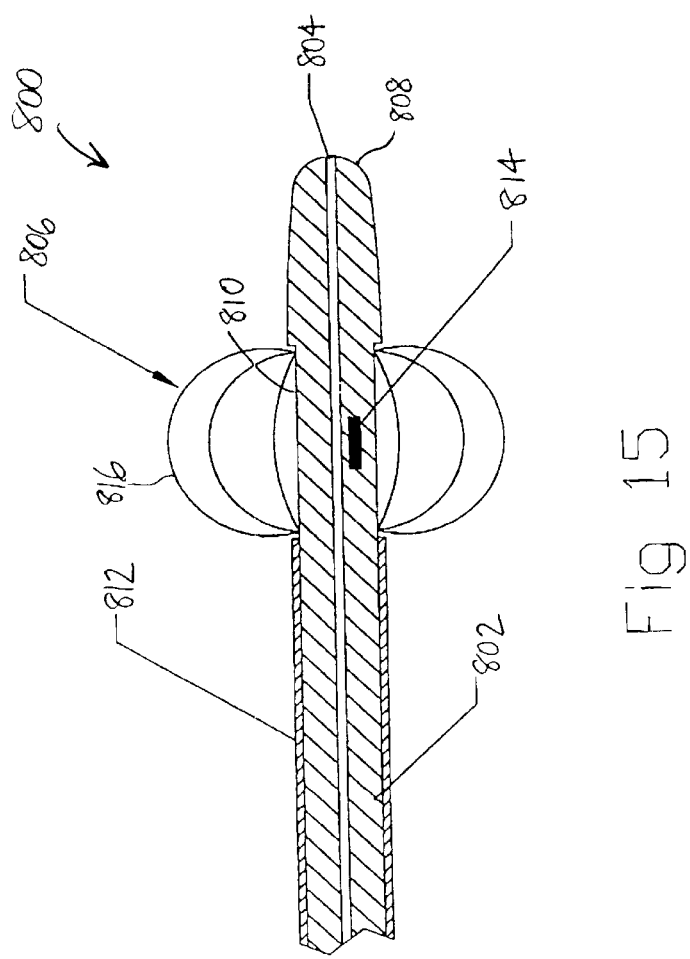
FIG. 15 is a partial longitudinal sectional view of the distal portion of a vessel expansion catheter device of the present invention having an expandable wire cage for expansion of the vessel.

An alternative vessel dilating catheter 800 of the present invention is shown in FIG. 15, and in use in FIG. 15a. The catheter 800 includes a catheter body 802 having a guidewire lumen 804 extending therethrough. A self-expandable dilation member 806 is mounted near a distal end 808 of the catheter body 802, typically within a recess 810. A retractable sheath 812 is adapted to slide axially over the catheter body 802 and acts to alternately conceal and deploy the dilation member 806. That is, the sheath 812 is shown in its retracted position permitting expansion of the dilation member 806. Distal movement of the sheath 812 causes the dilation member 806 to radially constrict into the recess 810. Optionally, an imageable marker 814 may also be provided in the catheter body 802 at the location of the dilation member 806.

The dilation member 806 may take a variety of forms, and may be deployed in other ways than by being spring biased outward. Indeed, those of skill in the art will understand that FIG. 15 is schematic and represents any number of dilation members that are attached to the catheter body 802 in a retracted state, and can be radially expanded to contact the inner wall of a vessel in which the catheter device 800 is positioned. The size of the dilation member 806 is such that the vessel wall becomes dilated, which facilitates imaging and penetration thereof, as described above.

In one embodiment, the dilation member 806 comprises an expandable cage having a plurality of individual struts 816 extending outward from the catheter body 802. The struts 816 are sized and arranged to outwardly dilate the vessel in which they are expanded. At a minimum, there will be three such struts 816. The struts 816 are distributed around catheter body 802 in such manner as to provide relief regions therebetween. That is, the circumferential spaces between the struts 816 provide relief regions to permit passage of a penetrating element, such as element 830 in FIG. 15a, into the target vessel 832. Desirably, the struts 816 are relatively thin so as to maximize the relief regions. As a result, the target vessel 832 is dilated by the dilation member 806, facilitating imaging of the target vessel at that location by the penetrating catheter 834.

In a further alternative embodiment of the present invention that is not illustrated, the dilation member may comprise an implantable stent deployed by the catheter. The stent may be constructed generally similarly to conventional stents, but with a relief area defined thereon for receiving the penetrating element therethrough into the target vessel. That is, for example, the stent may be a tubular body having a plurality of apertures in the expanded state, with at least one aperture larger than the rest and defining the relief area. There may be more than one relief area aperture disposed in a longitudinal line along the tubular body to accommodate some axial mis-aiming of the penetrating elements. Alternatively, a plurality of relief area apertures may be disposed around a circumference of the tubular body so that rotational orientation of the tubular body during implantation is less critical.

Examples of Methods and Procedures

The tissue penetrating catheters 11 and 11a may be used in conjunction with the vessel dilation catheter 200, 300, 400, 500, 600, 700, 800 shown in FIGS. 9–15a and described above or with any other vessel occlusion means as described above, to perform procedures where a penetration is made from the lumen of an artery or vein into the lumen of a target vessel including, as described in detail herebelow, a Percutaneous In Situ Coronary Artery Bypass (PICAB)

procedure as well as a Percutaneous In Situ Coronary Venous Arterialization (PICVA) procedure.

i. A Preferred Method for Performing the PICVA™ Procedure with Dilation of the Target Vein The PICVA™ procedure is useable to effectively provide arterial perfusion of an ischemic region of myocardium, even in cases where a coronary artery is so extensively obstructed that no patent distal portion of the artery remains available to carry bypassed arterial flow.

Figure 7A:
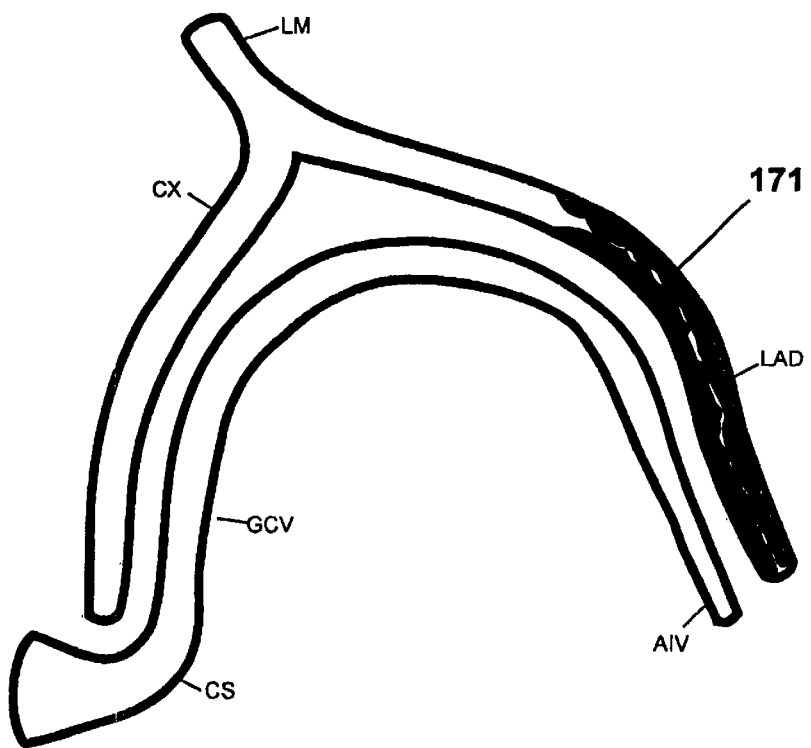
FIGS. 7a–8d illustrate the triangle of Brock-Moscheau (an anatomical term defining certain coronary arteries and coronary veins of the human heart) and showing by way of example certain coronary revascularation procedures that can be carried out in accordance with the teachings of this invention.

FIG. 7a is a diagram of a portion of the coronary vasculature known as known as the Triangle of Brouck-Moscheau. The Triangle of Brock-Moscheau is defined by the left anterior descending coronary artery LAD, the circumflex coronary artery CX, the anterior inter ventricular vein AIV. The arteries CX and LAD are both joined to and receive blood from the left main artery. The great coronary vein GCV forms a downwardly opening U-shaped configuration with the legs of the U being adjacent to arteries CX and LAD. Obstructions resulting from a build up of plaque may be found in either or both of the arteries CX and LAD. For example and for purposes of illustrating a preferred embodiment of the method of this invention, FIG. 7a shows an obstruction 171 in the left anterior descending artery LAD.

Figure 7B:
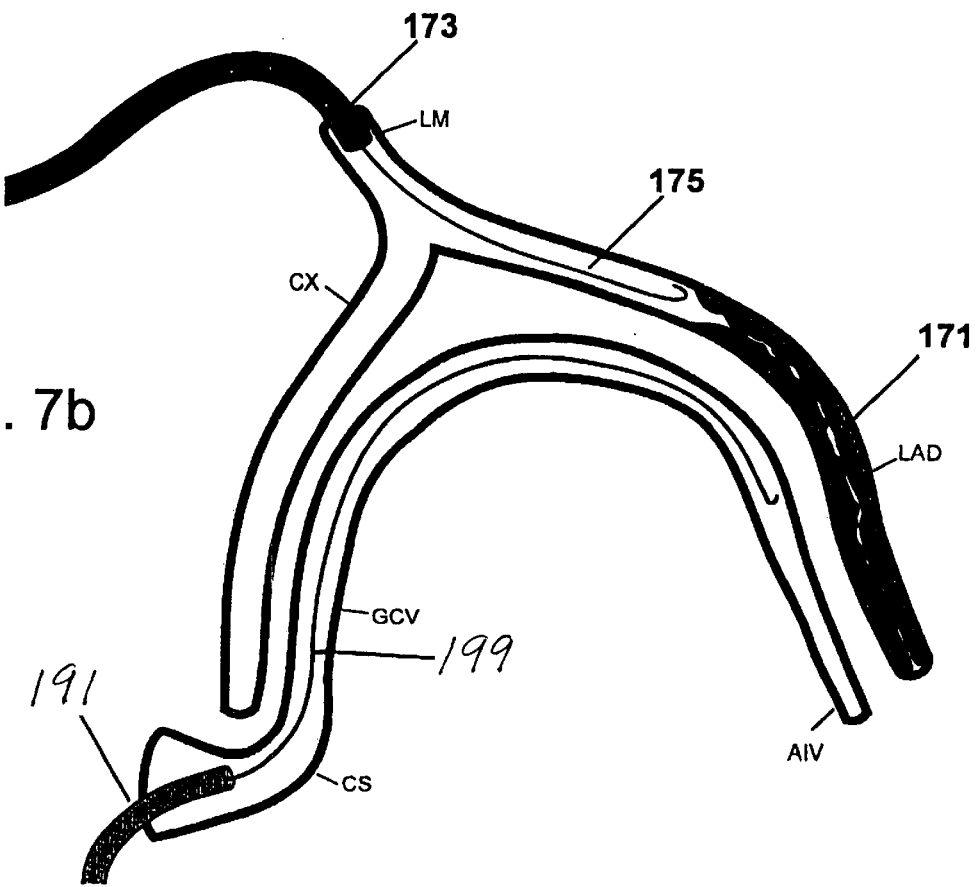

In the first step of the procedure, shown in FIG. 7b, a coronary guide catheter 173 is advanced into the left coronary ostium and a guidewire 175 such as a 0.014 inch guidewire is advanced through the guide catheter 173 into the lumen 176 of the left anterior descending artery (LAD) to a location just proximal of the obstruction 171 as shown in FIG. 7b. Also, a coronary venous sinus guide catheter 191 is advanced over a guidewire 194 into the coronary venous sinus CS. The guidewiare 194 is then further advanced through the coronary sinus guide catheter 191 through the great cardiac vein GCV and into the anterior inter ventricular vein AIV, as shown.

Figure 7C:
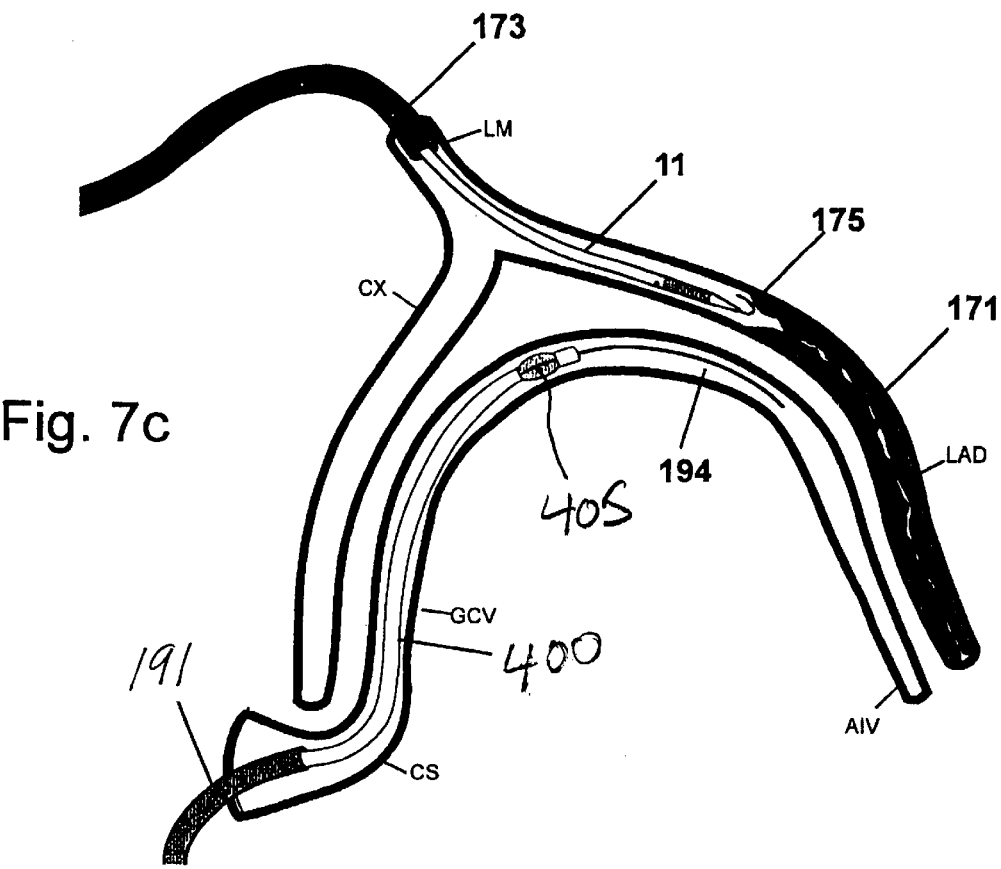

Next, in this example as shown in FIG. 7c, a subselective guide catheter or sheath 400 of the type shown in FIGS. 9 and 10 is advanced over guidewire 194 into the great cardiac vein GCV such that its balloon 405 is located proximal to the location at which the penetration is to enter the AIV. The tissue penetrating catheter 11 is percutaneously inserted and transluminally advanced through the guide catheter 173 and over the guidewire 175 into the left anterior descending artery LAD to a location just proximal of the obstruction 171 (FIG. 7c). The axial position of the guidewire 175 and of the catheter 11 within the artery LAD is known by conventional techniques which may include, for example, fluoroscopy of a radiopaque marker 33. Although this procedure is described with reference to the penetrating catheter 11, it should be understood that an identical procedure would be followed for another type of penetrating catheter 11a or those shown and described in the other patent and patent applications referred to hereabove.

Figure 7D:
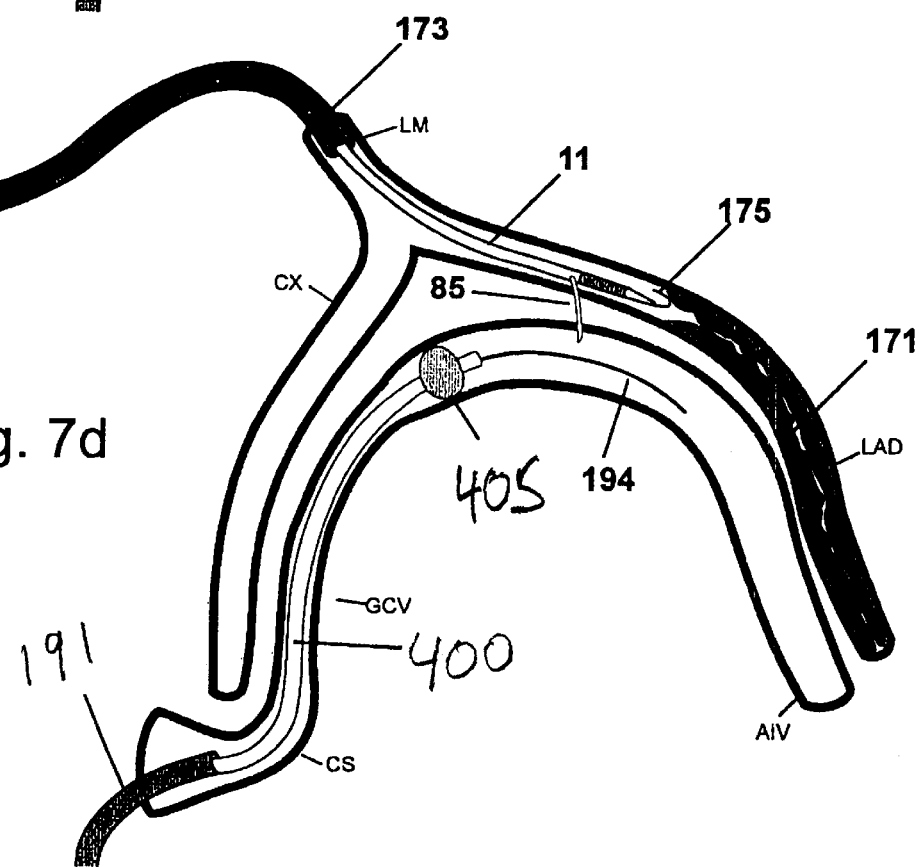

As shown in FIG. 7d, the balloon 405 is inflated to occlude venous blood flow through the AIV, thereby causing the AIV to dilate (e.g., the pressure of blood within the lumen of the vein increases thereby exerting outwardly directed radial pressure against the wall of the vein causing the vein to dilate to a larger diameter), as shown. with the penetrating catheter 11 in position within the LAD, the leads 85 are coupled to the imaging console 89 and the imaging transducer 81 is actuated to obtain images of the dilated portion of the AIV as shown, by way of example, in FIG. 6a. The penetrating catheter 11 is then moved longitudinally and/or rotated within the artery LAD, as required to cause the exit port 29 and hence a penetrator path indication or path region 148 to become aimed at the lumen of the dilated vein AIV. Such positioning an orientation of the penetration catheter 11 main, as described your above, be facilitated by use of one or more imaging techniques such as fluoroscopy and/or alter sound imaging of the target vessel. In this regard, it will be appreciated that because the target AIV has been dilated its image will be larger and more visible. Also, in cases where ultrasonic imaging of the target AIV is used, the wall of the dilated region of the AIV will appear with improved definition on the ultrasound image because the echogenicity of that vessel wall has been enhanced by the dilation-induced increase in tautness of the vessel wall. At this point, the tissue penetrator 85 is advanced through the exit opening 29 from the penetrating catheter 11 through the wall of the artery LAD, through any tissue that may be located between the artery LAD and vein AIV, through the wall of the dilated region of vein AIV and into the lumen 177 of the vein AIV, upstream of the obstruction 171, as shown in FIG. 7d. As discussed above, the ability of the penetrator 85 to penetrate through the dilated wall of the vein AIV is enhanced due to the tautness of the dilated vein wall. Also, because of the occlusion of the vein AIV by balloon 405, the blood pressure within the vein AIV has increased to somewhere near the pressure of blood within the artery LAD. Thus, the difference in blood pressure between the artery LED and vein AIV is minimized, thereby avoiding any turbulent or sudden surge of arterial blood into the vein AIV as the penetrator 85 enters the lumen of the vein AIV.

Figure 7E:
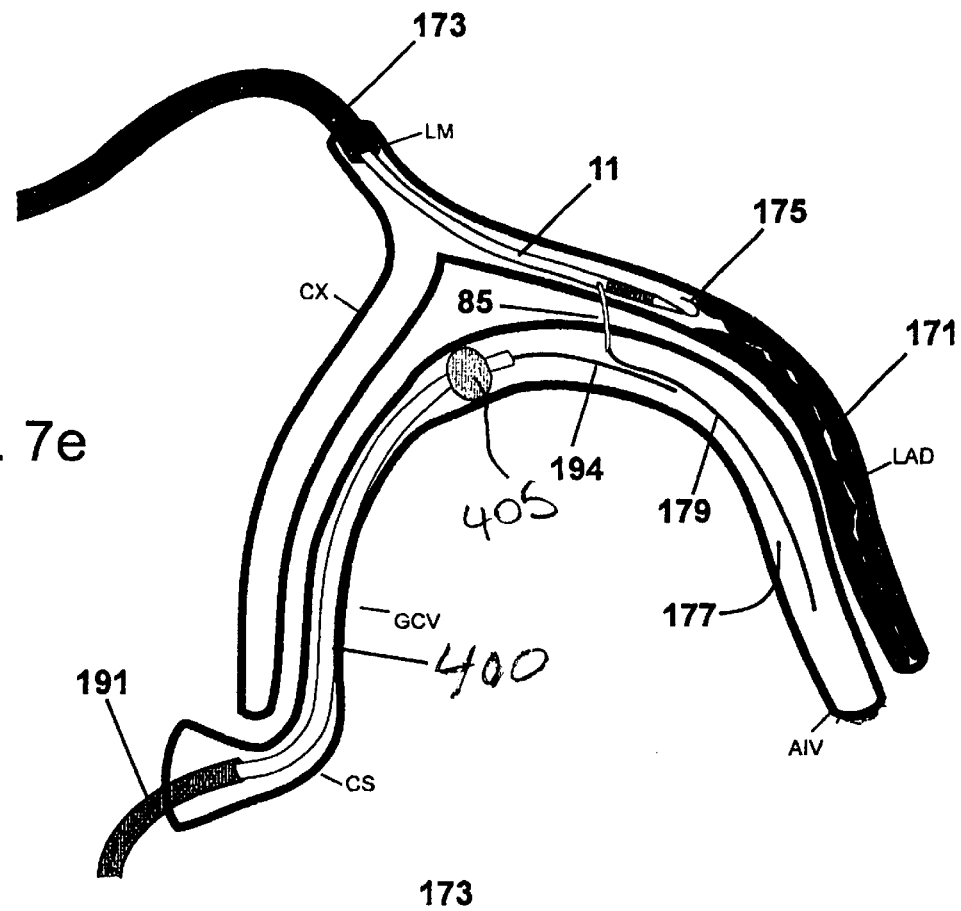

As shown in FIG. 7e, with the balloon 405 still inflated and the AIV still dilated, and with the penetrating catheter 11 and the tissue penetrator 85 still in the position shown in FIG. 7d, a first crossing guidewire 179 is advanced through the lumen 851 of the tissue penetrator 85 and into the lumen 177 of the vein AIV. Advancement of the crossing guidewire 179 through the lumen of the AIV may be made easier by the fact that that portion of the AIV has been dilated. The tissue penetrator 85 is then retracted into the catheter 11 leaving the crossing guidewire 179 in place such that it extends from the lumen 176 of the artery LAD into the dilated lumen 177 of the vein AIV.

Figure 7F:
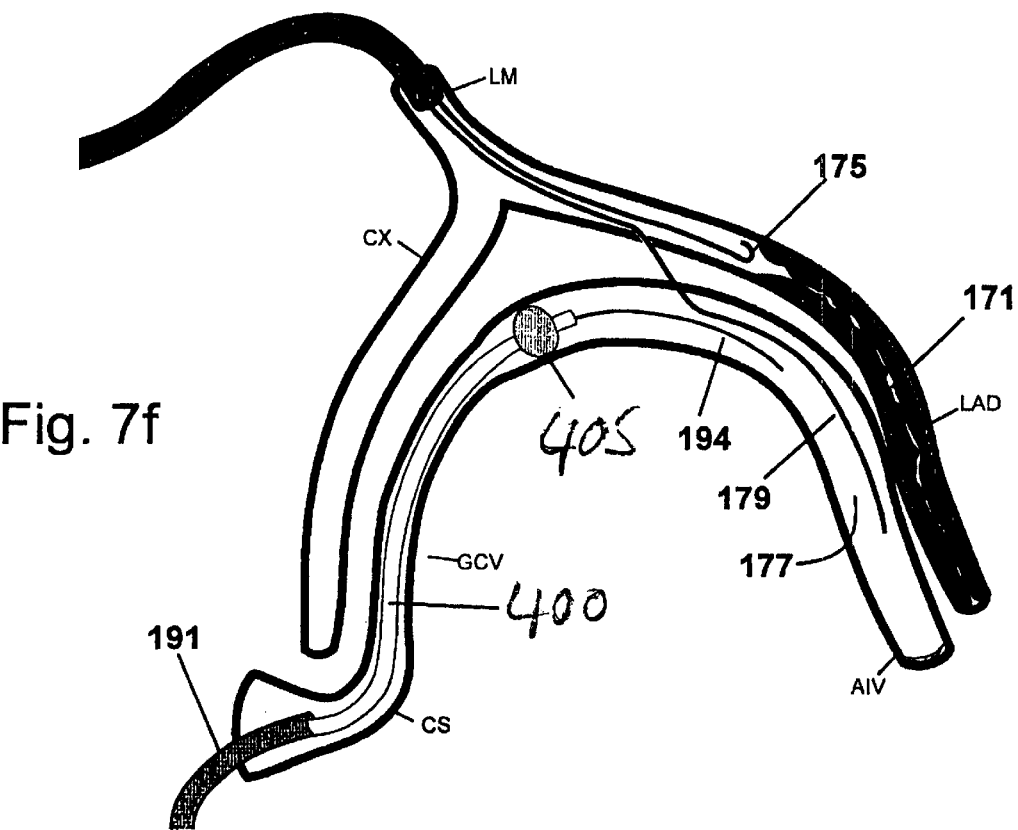

As shown in FIG. 7f, the penetrating catheter 11 is then removed by retracting it back over the guidewire 175 and out through the guide catheter 173 leaving the guidewires 175 and 179 in place. Also, while the balloon 405 of the subselective sheath 400 remains inflated and the AIV will remain dilated.

Figure 7G:
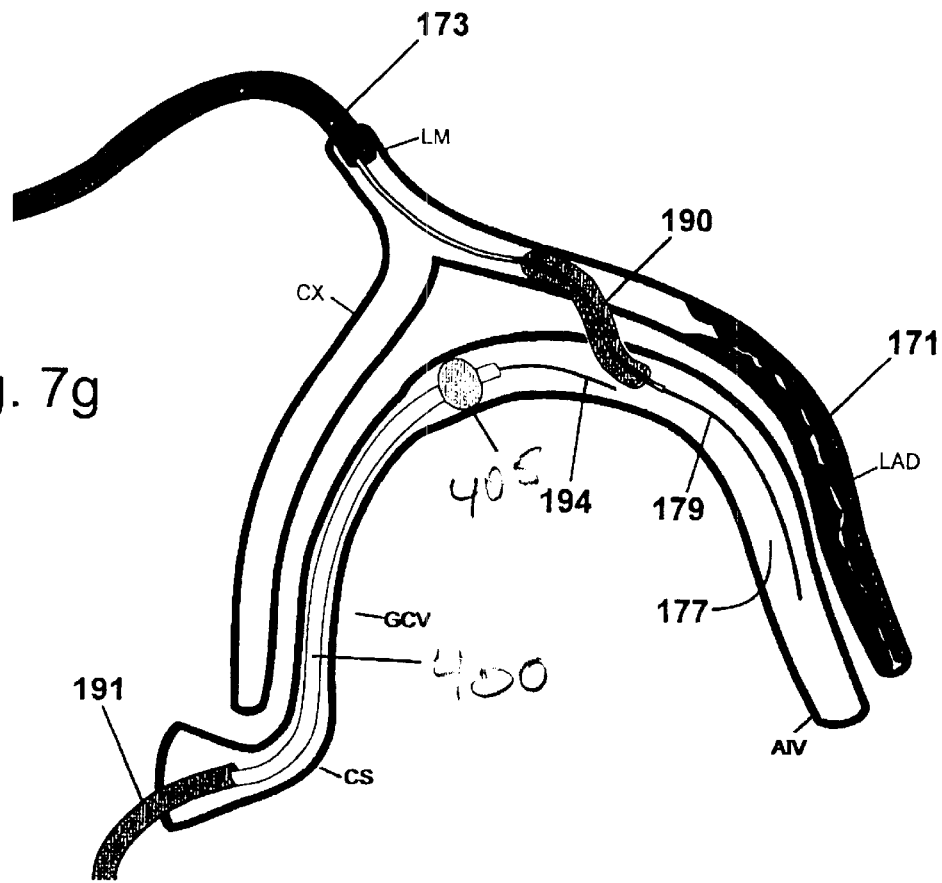

Thereafter, as shown in FIG. 7g, if it is necessary to enlarge or modify the penetration tract created by the penetrator 85, a tract modification or enlargement apparatus 190 may be advanced over the first crossing guidewire 179 to enlarge or otherwise modify the penetration tract. This tract modifying apparatus 190 may comprise a balloon catheter or radiofrequency tissue severing device as described in U.S. patent application Ser. No. 09/056,589, the entirety of which is expressly incorporated herein by reference.

Figure 7H:
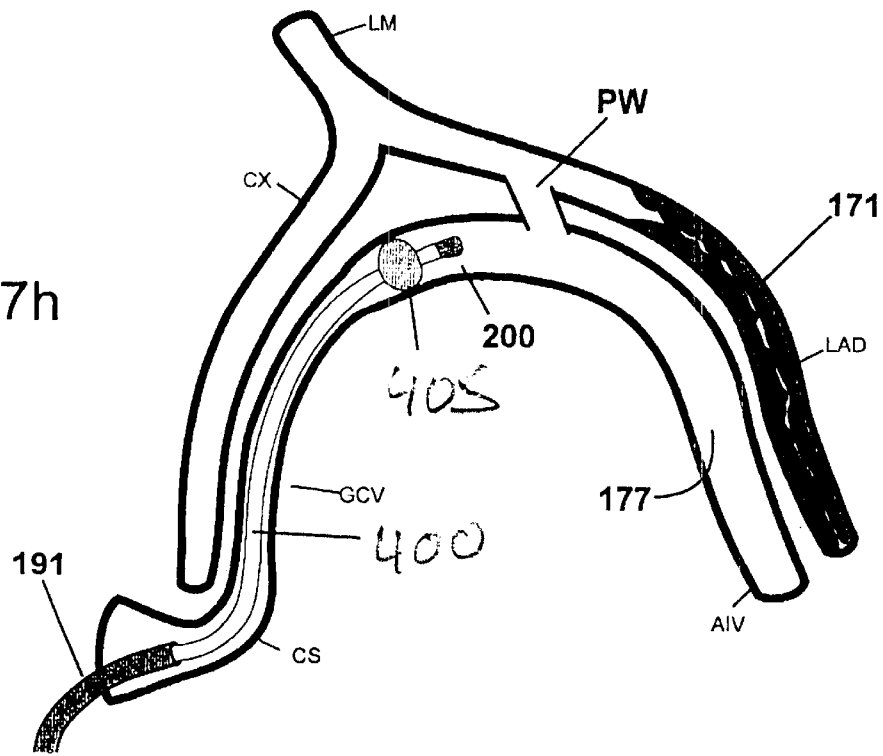

As shown in FIG. 7h, after any necessary enlargement or modification of the penetration tract has been complete, the tract modifying apparatus 190 and first crossing guidewire 179 are removed, leaving open the passageway PW between the artery LAD and vein GCV/AIV. Because the balloon 405 remains inflated within the vein AIV at a location proximal to the passageway PW, arterial blood that enters the lumen 177 of the vein AIV through the passageway PW will not pulse or flow through the vein in the proximal direction beyond the inflated balloon 405, thereby avoiding undesirable steal all of arterial blood during the procedure.

At this stage of the procedure, it is desired to introduce a permanent blocker or occluder into the lumen of the vein AIV, proximal to the passageway PW, such that the balloon 405 maybe if the inflated and the subselective sheath 400 removed. To facilitate this, with the balloon 405 remaining inflated and the vein AIV remaining dilated, and intravascular ultrasound imaging catheter (IVUS) is advanced into a lumen of the subselective sheath 400 to a location distal of the balloon 405, and the IVUS catheter is used to obtain a distinct image of the wall of the dilated region of vein AIV. This image will then be used to obtain a precise measurement of the diameter of the vein AIV in its dilated state. A radially expandable, implantable blocker 200 of appropriate size is then selected based on the measurement of the dilated diameter of the vein AIV obtained using the IVUS catheter. Thereafter, if the IVUS catheter has been inserted into the through lumen of the subselective sheath 400 that opens through its distal end, the IVUS will be removed from the lumen of the subselective sheath 400, and the selected radially expandable blocker 200 is introduced to the proximal and the subselective sheath 400 into lumen thereof. (Alternatively, in some cases the IVUS may be placed within a second or sealed lumen of the subselective sheath 400 such that the blocker 200 may be introduced and passed through the sheath's through lumen without requiring retraction and removal of the IVUS. One example of a subselective sheath having such a sealed lumen is described in U.S. patent application Ser. No. 09/505,149 entitled Sterility Barriers for Insertion of Non-Sterile Apparatus Into Catheters or Other Medical Devices filed on Feb. 15, 2000.) A pusher (not shown) is then used to push the radially collapsed blocker through the lumen of the subselective sheath 400 and out of its distal end, as shown in FIG. 7h. The blocker 200 then self expands to the diameter of the dilated vein lumen and frictionally engages the wall of the vein AIV such that the blocker is held in a fixed location and will permanently block (fully or partially) blood flow in the proximal direction through the vein AIV, as shown in FIG. 7K.

Figure 7K:
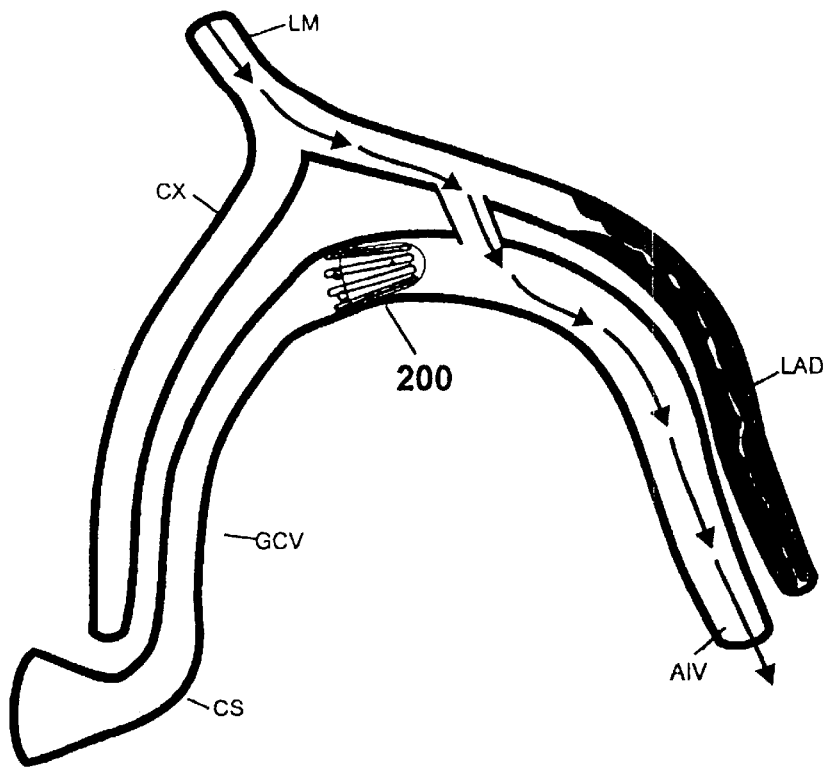

Thereafter, as shown in FIG. 7k, the balloon 405 is deflated and the subselective sheath 400 and coronary guide catheter 191 are removed. This completes the PICVA procedure, allowing arterial blood to flow from the artery LAD, through the passageway PW and into the vein GCV/AIV where it flows in the direction opposite normal venous return so as to retro-perfuse the ischemic myocardium through the coronary vein(s).

ii. A Preferred Method for Performing the PICAB Procedure

FIGS. 8a–8d show, in step-by-step fashion, an example of the manner in which a two channel PICAB procedure may be performed, or in the alternative, how the above-described PICVA procedure (FIGS. 7a–7k) may be converted into a two-channel PICAB procedure. This PICAB procedure will typically be used in cases where the obstruction 171a does not extend into the distal LAD and thus, a patent distal LAD is available to carry blood flow to the ischemic myocarduim.

Figure 8A:
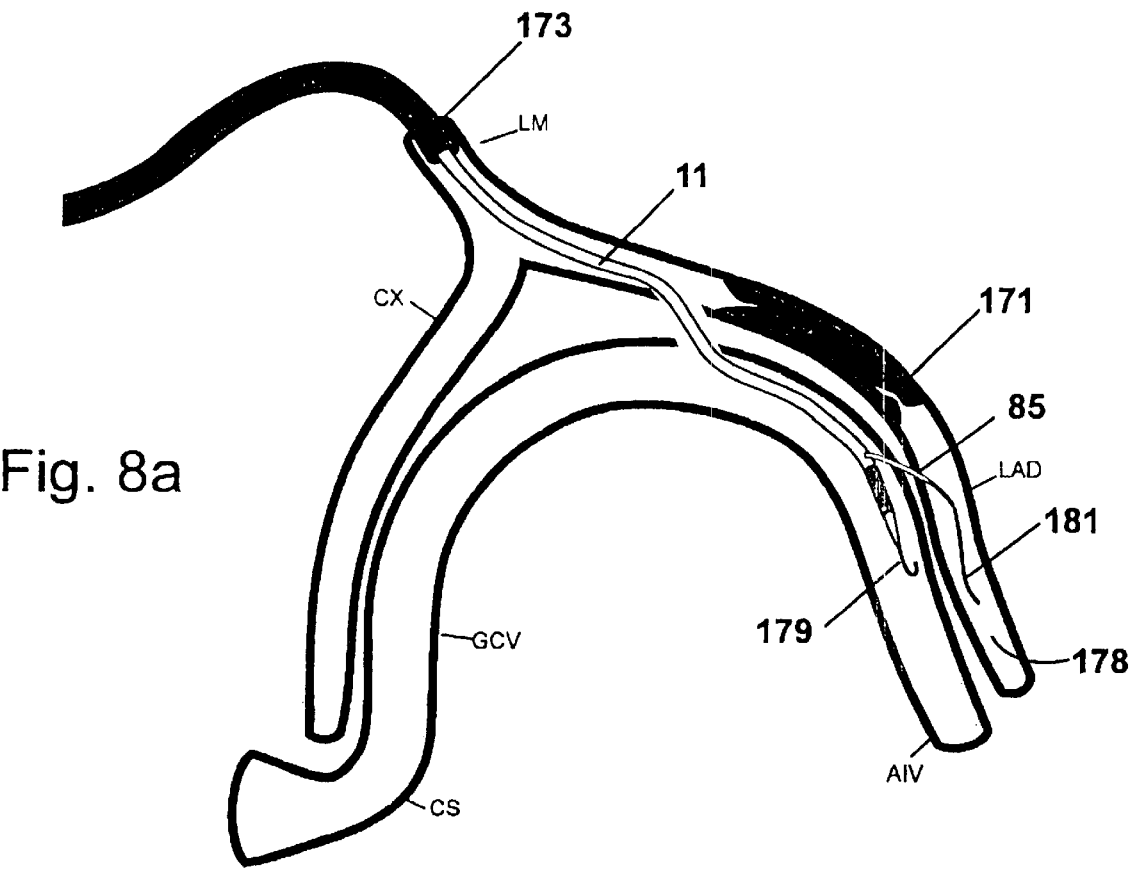

As shown in FIG. 8a, if the two channel PICAB technique is to be employed then in lieu of the placement of the embolic blocker 200 being placed (starting from the step referenced in FIG. 7g) the guidewire 175 is withdrawn and the catheter 11 is advanced over the crossing guidewire 179 to the position shown in FIG. 8a. To accomplish this, the tissue penetrator is retracted over the crossing guidewire 189 to remove the first crossing guidewire from the tissue penetrator 85 and then the crossing guidewire 179 is introduced into the main guidewire lumen 35 of the catheter 11. Consequently, the catheter 11 can be advanced over the crossing guidewire 179 to the position of FIG. 8a wherein the catheter extends through the lumen 176 of the artery LAD, through the openings created in the walls of the artery LAD and the vein AIV and into the lumen 177 of the vein AIV. The longitudinal or axial position of the catheter 11 in the vein AIV relative to the obstruction 171 is known using conventional techniques. With the catheter 11 in the position shown in FIG. 8a, the imaging transducer 81 is again actuated and the catheter 11 is rotated within the vein AIV as required and as explained above in connection with FIGS. 6a and 6b to cause the penetrator path indication to be aimed at the lumen of the artery LAD at a location downstream of the obstruction 171. With the penetrator path indication and the exit port 29 properly aimed at the artery 171, the tissue penetrator 85 is advanced from the catheter 11 through the walls of the vein AIV and the artery LAD and into the lumen of the artery LAD as shown in FIG. 8a. Also, as shown, a second crossing guidewire 181 is advanced through the lumen 85L of the tissue penetrator 85 and into the lumen of the artery LAD.

Figure 8B:
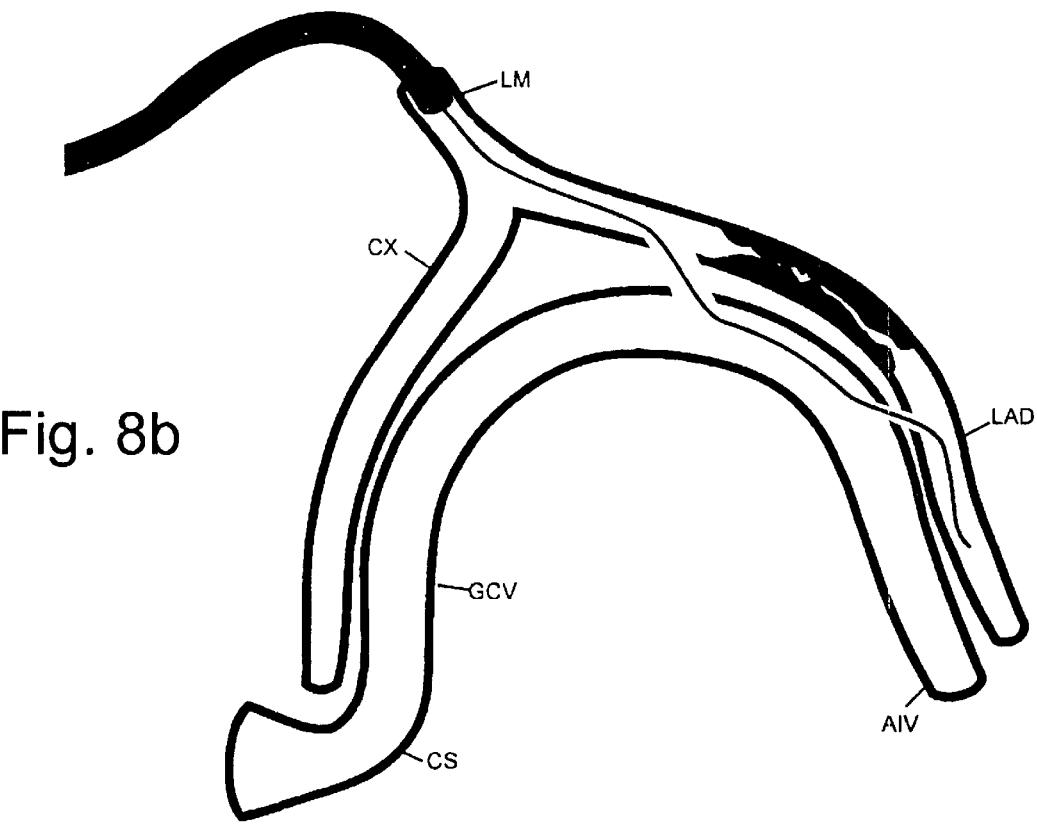

As shown in FIG. 8b, the tissue penetrator 85 is then retracted into the catheter 11 leaving the second crossing guidewire 181 in the artery LAD. The catheter 11 and the first crossing guidewire 179 are then removed leaving the second crossing guidewire 181 in place such that it extends from the artery LAD into the lumen 177 of the vein AIV and back into the artery LAD as shown in FIG. 8b.

Figure 8C:
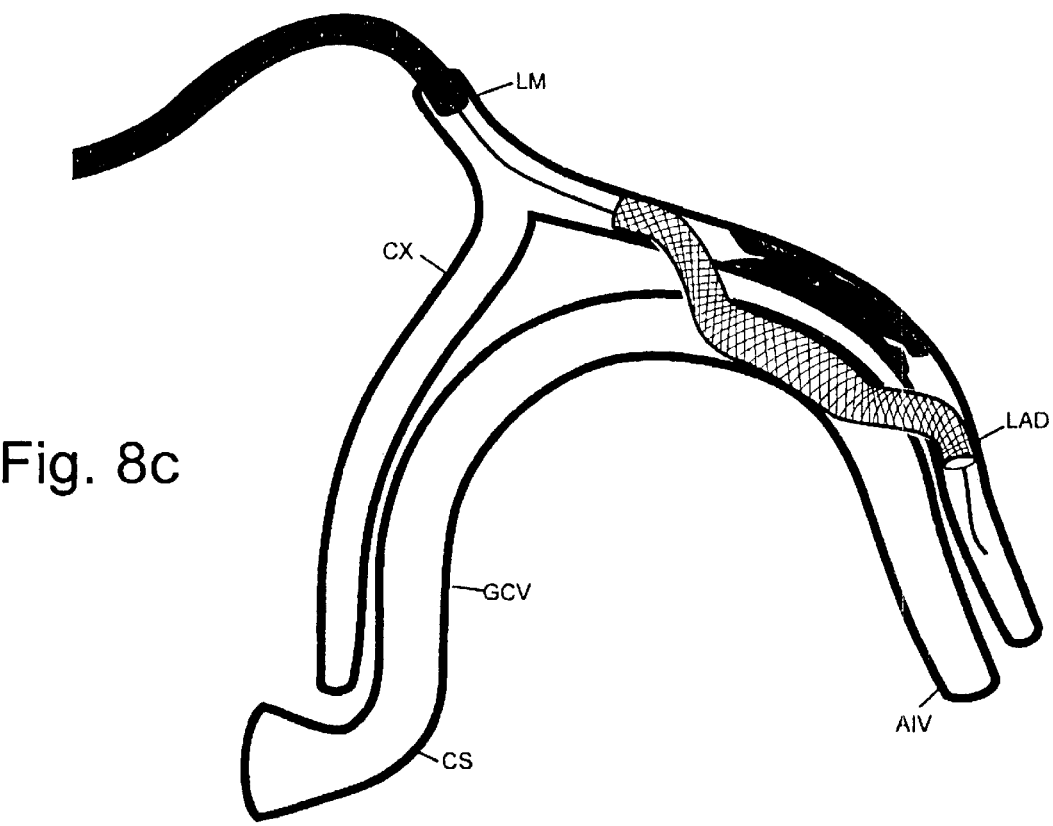
Figure 8D:
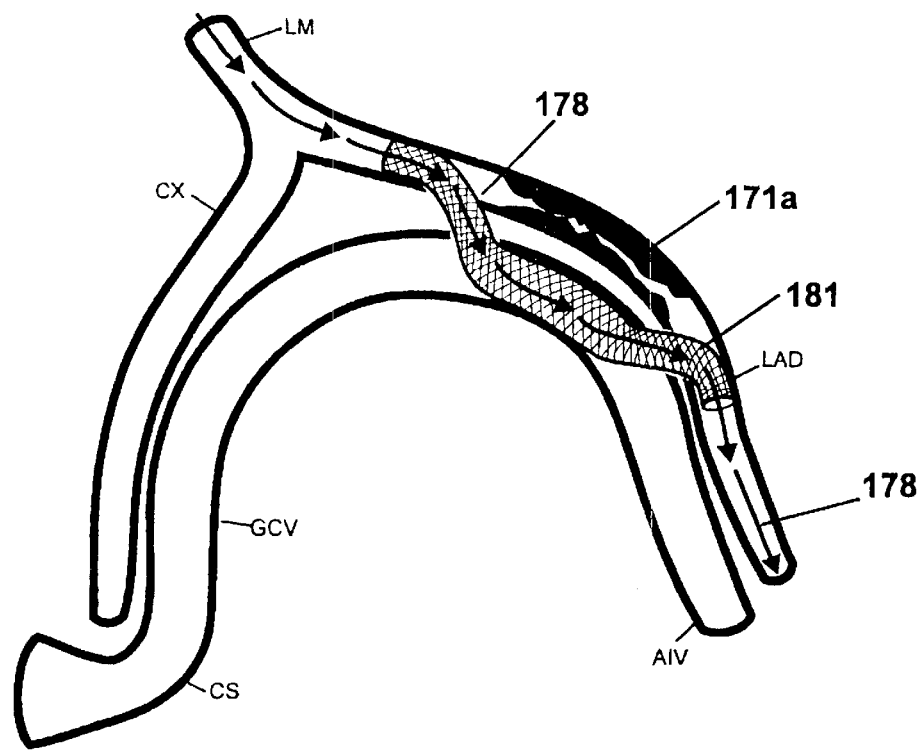

To create a blood flow channel around the obstruction 171, an expandable connector 191 may be employed. As shown in FIGS. 8c and 8d, the connector 191 is implanted such that the connector extends from the artery LAD through the openings created in the walls of the artery LAD and the vein AIV, through the lumen 177 of the vein AIV, through the openings created in the walls of the vein and artery LAD distally of the obstruction 171 and back into the artery LAD. The expandable connector may be implanted, for example, by utilizing a connector delivery catheter (not shown) and advancing such connector delivery catheter over the second crossing guidewire 181. After implantation of the connector 191, the second crossing guidewire is withdrawn and so is the guide catheter 173. It will be appreciated that instead of deploying one expandable connector, it may be preferred to employ two shorter connectors (not shown) at each of the first and second crossing sites. In this approach, a proximal and distal embolic blocker may be required to be placed in the vein proximal to the first crossing site (in the GCV) and distal to the second crossing site (in the AIV) to complete the bypass circuit.

Although exemplary embodiments of the invention have been shown and described, many changes, modifications and substitutions may be made by those having ordinary skill in the art without necessarily departing from the spirit and scope of this invention. For example, where this patent application has listed the steps of a method or procedure in a specific order, it may be possible (or even expedient in certain circumstances) to change the order in which some steps are performed, and it is intended that the particular steps of the method or procedure claims set forth herebelow not be construed as being order-specific unless such order specificity is expressly stated in the claim. Another example is that, although the specific procedures described in detail in this application may involve penetrating through an "acceptable penetration zone," such acceptable penetration zone need not be occupied by tissue but rather such acceptable penetration zone may fully or partially comprise an open space such as a body cavity or void. Accordingly, it is intended that all such additions, deletions, modifications and variations be included within the scope of the following claims.

What is claimed is:

1. A method for locating a target blood vessel of a patient and penetrating the target vessel with a penetrating element, comprising:

providing a transluminally insertable tissue penetration device having a penetrating element thereon passable through the wall of a target blood vessel from the exterior thereof;

providing an imaging apparatus for locating a target blood vessel;

causing at least a target region of the target vessel to dilate;

locating the target region of the target vessel using the imaging apparatus;

transluminally positioning the tissue penetration device within a blood vessel or internal body cavity adjacent the target vessel such that the penetrating element is aimed at the dilated target region;

passing the aimed penetrating element from the penetration device through the wall of the target blood vessel.

2. The method of claim 1, wherein the tissue penetration device is a tissue penetration catheter, and wherein the step of positioning comprises transluminally advancing the tissue penetration catheter through the vasculature of the patient into a blood vessel adjacent the target vessel.

3. The method of claim 1, wherein the tissue penetration device is a tissue penetration catheter, and wherein the step of positioning comprises advancing the tissue penetration catheter into a body cavity adjacent the target vessel.

4. The method of claim 1, wherein the imaging apparatus is located on the tissue penetration device.

5. The method of claim 1, wherein the "causing" step comprises:

providing a vessel occlusion catheter that has an occluder formed thereon;

positioning the vessel occlusion catheter within the patient's vasculature associated with the target vessel; and, using the occluder of the vessel and occlusion catheter to at least partially occlude a portion of the vasculature in which it is positioned, thereby causing dilation of at least a portion of the target vessel.

6. The method of claim 1, wherein the "causing" step comprises:

providing a vessel dilation catheter that has an enlargeable member that is alternately disposable in a compact configuration and an enlarged configuration;

placing the vessel dilation catheter in the patient's vasculature associated with the target vessel such that the enlargeable member is located in the target vessel; and enlarging the enlargeable member to cause dilation of the target vessel.

7. The method of claim 1, wherein the "causing" step:

providing a double occlusion catheter having a proximal occluder and a distal occluder at spaced apart locations thereon;

using the proximal and distal occluders to occlude the lumen of the target vessel at first and second locations; and, infusing a fluid into the lumen of the target vessel between the proximal and distal occluders to dilate the portion of the target vessel located between said first and second locations.

8. The method of claim 1, wherein the step of causing comprises:

providing a double dilator catheter having a proximal dilator and a distal dilator at spaced apart locations thereon;

using the proximal and distal dilators to dilate the target region of the target vessel between the first and second locations.

9. The method of claim 1, wherein the step of causing comprises:

providing a dilation catheter having a catheter body and a dilation member thereon, the dilation member initially provided on the catheter body in a retracted state to permit advancement of the catheter body so that the dilation member is located in the target vessel, the dilation member being expandable from the retracted state to dilate a target region of the target vessel, the dilation member including a relief area for passage of the penetrating element;

positioning the dilation catheter in the target region of the target vessel; and expanding the dilation member in the target region of the target vessel.

10. A percutaneous, transluminal method for penetrating from a host vessel into a target vessel, said method comprising the steps of:

a. providing a tissue penetration catheter that is advanceable into the lumen of a host vessel and has a penetrator that is advanceable laterally therefrom said penetrator comprising an elongate member having a lumen extending therethrough;

b. transluminally advancing the tissue penetrating catheter into the host vessel;

c. causing at least a target region of the target vessel to dilate;

d. positioning the tissue penetrating catheter such that its penetrator is aimed at the dilated target region of the target vessel;

e. passing the penetrator from the tissue penetrating catheter, through the wall of the host vessel, through the wall of the target vessel and into the lumen of the target vessel at the target region;

f. passing a guide wire through the lumen of the penetrator and into the lumen of the target vessel; and, g. retracting the tissue penetrator into the tissue penetrating catheter leaving the guidewire in place such that it extends from the lumen of the artery into the lumen of the target vessel.

11. A method according to claim 10 wherein the step of causing at least a target region of the target vessel to dilate comprises:

providing a vessel occlusion catheter that has an occluder formed thereon;

positioning the vessel occlusion catheter within the patient's vasculature associated with the target vessel; and, using the occluder of the vessel and occlusion catheter to at least partially occlude a portion of the vasculature in which it is positioned, thereby causing dilation of at least a portion of the target vessel.

12. A method according to claim 11 wherein the occluder comprises a balloon and wherein the step of "using the occluder" comprises inflating the balloon.

13. A method according to claim 11 wherein the host vessel is an artery, and wherein it is desired to cause arterial blood to flow from the artery into the target vessel, and wherein the method further comprises the step of:

enlarging the penetration tract, created by passing the penetrator from the tissue penetrating catheter between the artery and the target vessel, to create a blood flow channel through which blood may flow from the artery and into the target vessel.

14. A method according to claim 10 wherein the step of causing at least a target region of the target vessel to dilate comprises:

providing a vessel dilation catheter that has an enlargeable member that is alternately disposable in a compact configuration and an enlarged configuration;

placing the vessel dilation catheter in the patient's vasculature associated with the target vessel such that the enlargeable member is located in the target vessel; and enlarging the enlargeable member to cause dilation of the target vessel.

15. A method according to claim 14 wherein the target vessel is a target vein, the method further comprises the step of:

implanting an occluder to at least partially occlude a vein to cause arterial blood that enters the target vein through the blood flow channel to subsequently flow through the target vein in a direction opposite normal venous flow.

16. A method according to claim 10 wherein the step of causing at least a target region of the target vessel to dilate comprises:

providing a double occlusion catheter having a proximal occluder and a distal occluder at spaced apart locations thereon;

using the proximal and distal occluders to occlude the lumen of the target vessel at first and second locations; and, infusing a fluid into the lumen of the target vessel between the proximal and distal occluders to dilate the portion of the target vessel located between said first and second locations.

17. A method according to claim 16 wherein the double occlusion catheter further comprises a first perfusion opening formed in the catheter at a location proximal to the proximal occluder, a second perfusion opening formed in the catheter at a location distal to the distal occluder and a perfusion lumen that extends through the catheter between the first and second perfusion openings such that when the occluders are occluding the lumen of the target vessel and, blood may flow in one of the perfusion openings, through the perfusion lumen and out of the other perfusion opening and wherein the method further comprises allowing blood to flow in one of the perfusion openings, through the perfusion lumen and out of the other perfusion opening while the lumen of the target vessel is occluded by the occluders.

18. A method according to claim 16 wherein the target vessel is a target vein, and wherein the step of causing at least a target region of the target vessel to dilate comprises:

providing a venous occlusion/blocker delivery catheter that has a temporary venous occluder formed thereon and is capable of implanting a permanent vein occluder into the lumen of the vein in which it is positioned;

positioning the venous occlusion/blocker delivery catheter within a vein; and, using the temporary vein occluder to at least partially occlude the vein in which the venous occlusion catheter is positioned, thereby causing temporary dilation of at least a portion of the target vein;

and wherein, after the step of passing the penetrator from the tissue penetrating catheter is completed, the method further comprises;

terminating the temporary occlusion of the vein commenced in the step of causing at least a target region of the target vessel to dilate thereby allowing the target vein to return to a non-dilated state; and, using the venous occlusion/blocker delivery catheter to implant a permanent vein blocker in the lumen of a vein to cause arterial blood that enters the target vein through the blood flow channel to flow through the target vein in a direction opposite normal venous blood flow.

19. A method according to claim 10 wherein the target vessel is a target vein, the method further comprising:

repositioning the tissue penetrating catheter to a second location and causing the penetrator to advance a second time to form a second penetration tract between the target vein and an artery; and, enlarging the second penetration tract to form a second blood flow channel through which arterial blood that has entered the target vein through the blood flow channel will pass from the target vein, through the second blood flow channel and into an artery.

20. A method according to claim 10 further comprising the step of:

imaging a dilated portion of the target vessel while the occlusion of the step of causing at least a target region of the target vessel to dilate is being performed and using the image so obtained to aim the penetrating catheter such that its penetrator will pass from the penetrating catheter into the dilated region of the target vessel.

21. A method according to claim 20 wherein an imaging apparatus is associated with the penetrating catheter and wherein the imaging of the target vessel is carried out using that imaging apparatus.

* * * * *